(12) United States Patent
Nguyen et al.

(10) Patent No.: US 11,426,714 B2
(45) Date of Patent: Aug. 30, 2022

(54) METAL ORGANIC FRAMEWORKS (MOFS) AND METHODS OF SYNTHESIZING AND USING THE SAME

(71) Applicants: Phuong Thi Kieu Nguyen, Ho Chi Minh (VN); Quang Thien Luong, Ho Chi Minh (VN); Thang Bach Phan, Ho Chi Minh (VN); Y Bach Nhu Tran, Ho Chi Minh (VN)

(72) Inventors: Phuong Thi Kieu Nguyen, Ho Chi Minh (VN); Quang Thien Luong, Ho Chi Minh (VN); Thang Bach Phan, Ho Chi Minh (VN); Y Bach Nhu Tran, Ho Chi Minh (VN)

(73) Assignees: VIETNAM NATIONAL UNIVERSITY HO CHI MINH CITY, Ho Chi Minh (VN); Center for Innovative Materials and Architectures, Ho Chi Minh (VN)

(*) Notice: Subject to any disclaimer, the term of this patent is extended or adjusted under 35 U.S.C. 154(b) by 0 days.

(21) Appl. No.: 16/699,777

(22) Filed: Dec. 2, 2019

(65) Prior Publication Data
US 2021/0162388 A1 Jun. 3, 2021

(51) Int. Cl.
| | |
|---|---|
| *B01J 31/10* | (2006.01) |
| *B01J 31/16* | (2006.01) |
| *B01J 35/10* | (2006.01) |
| *B01J 37/08* | (2006.01) |
| *B01J 20/22* | (2006.01) |
| *B01J 20/28* | (2006.01) |
| *B01J 20/30* | (2006.01) |

(52) U.S. Cl.
CPC ......... *B01J 31/1691* (2013.01); *B01J 20/226* (2013.01); *B01J 20/28083* (2013.01); *B01J 20/3085* (2013.01); *B01J 35/1061* (2013.01); *B01J 37/08* (2013.01); *B01J 2231/34* (2013.01); *B01J 2531/16* (2013.01); *B01J 2531/26* (2013.01); *B01J 2531/842* (2013.01); *B01J 2531/845* (2013.01); *B01J 2531/847* (2013.01)

(58) Field of Classification Search
None
See application file for complete search history.

(56) References Cited

U.S. PATENT DOCUMENTS

2014/0081044 A1* 3/2014 Maurer ................ C07C 69/94
562/475

OTHER PUBLICATIONS

Oh et al. (international Journal of Hydrogen Energy, 42, 2017, 1027-1035 (Year: 2017).*

* cited by examiner

*Primary Examiner* — Yun Qian

(57) ABSTRACT

A new metal organic framework (MOF) series and method of synthesizing the same are disclosed which includes an organic linking ligand having the formula:

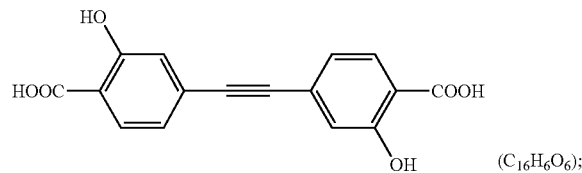

and a metal ion bonded to the organic linking ligand.

20 Claims, 26 Drawing Sheets

METAL ORGANIC FRAMEWORKS (MOFS) AND METHODS OF SYNTHESIZING AND USING THE SAME

FIELD OF THE INVENTION

The present invention relates generally to Metal Organic Frameworks (MOFs). More specifically, the present invention relates to new Metal Organic Frameworks (MOFs), their synthesis, and applications.

BACKGROUND ART

Currently, there exist some 85,000 Metal-Organic Framework (MOFs) in the market such as the MOF-74 series. These Metal-Organic Frameworks (MOFs) have exceptional porosity and reveal great promises in a wide range of applications including gas storage, separation, and catalysis. In particular, the development of new adsorbents and materials for energy-related applications such as fuel cells, supercapacitors, and catalytic conversions have made MOFs objects of extensive studies, industrial-scale production, and applications. Although the potentials of MOFs for gas capture and catalytic conversion have been extensively established, the discovery of new MOFs for effectively capture and separation of $CO_2$, as well as efficient transformation of $CO_2$ into valuable chemicals is still highly in demand.

There is particular attention in highly porous MOFs endowed with unsaturated metal sites, which are taking advantage of Lewis acidity afforded by partial positive charges on metal sites. MOFs are replete with these sites within the accessible pore apertures, which have been shown to enhance the $CO_2$ storage and catalytic conversion of $CO_2$. As such, the honeycomb-like structure of the well-known MOF-74 family, constructed from infinitely rod-shaped inorganic building units connected by 2,5-dioxidoterephthalate units, show one-dimensional hexagonal channels with coordinatively unsaturated metal sites in the non-interpenetrating structures [1]. This type of structure attributing large pore apertures permits easy access and dispersion of guest molecules, such as gases and small organic molecules, to the active metal units of the porous frameworks. In addition, the pore sizes, pore surface, and physical and chemical characteristics within such porous MOFs can be systematically modified by changing the component containing secondary building units (SBUs) and/or organic linker without changing the topological structure.

In 2012, two MOF-74 members, Co-MOF-74 and Mg-MOF-74, were first used as the heterogeneous catalysts for the styrene carbonate synthesis from the cycloaddition of $CO_2$ and styrene oxide with the conversion up to 95% in the presence of chlorobenzene, $CO_2$ pressure of 20 bar and temperature of 100° C. [2], [3]. In these works, the experimental $CO_2$ uptakes of Co-MOF-74 and Mg-MOF-74 were also found to be 182 cm$^3$/g and 146 cm$^3$/g respectively. The characteristic of open metal sites attributed to infinite metal-containing clusters of MOF-74's framework is a well-known structural feature for the highly desirable $CO_2$ adsorption and acting as Lewis acid sites catalyzed in the chemical fixation of $CO_2$, and other catalytic acid-promoted reactions. These discoveries allowed for the development of new isostructural materials with different metal-containing units (M=Mg, Ni, Co, Zn, Fe, Cu) for catalytic activity on $CO_2$ transformation which was not observed in the identical MOF-74's structure.

Another consideration of structural characteristic for effectively $CO_2$ conversion is the large hexagonal pore aperture which can enhance the diffusion of organic molecules and interaction between substrate molecules and catalytic sites. For example, a Zr-based framework, namely MOF-892, with the hexagonal pore metrics of 24×27 Angstrom Å$^2$ showed high conversion, selectivity, and yield (96, 86, 82%, respectively) for the cycloaddition of $CO_2$ under mild conditions: solvent-free, ambient pressure of $CO_2$, 80° C. for 16 hours [4]. A Hf-NU-1000 with has a hexagonal mesopore of 29 Å also exhibited highly catalytic $CO_2$ fixation (yield of 100%) under room temperature, 1 atm of $CO_2$, for 56 hours in the presence of acetonitrile solvent [5]. These discoveries permit for development of new hexagonal mesoporous frameworks for the efficiently catalytic chemical fixation of $CO_2$. Accordingly, there exist demands for new materials containing vary Lewis acidities which are taking advantage of different inorganic metal ions and having the large accessible pore apertures possess high surface area.

On the other hand, benzylic ethers have extensively used in organic chemistry as one of the protecting groups for alcohols or phenols. In particular, benzyl ethers can be effectively removed by common hydrogenation in the presence of $H_2$, and Raney Ni or Pd/C as the catalyst at an elevated temperature. Accordingly, there exists a need for the development of a safe and facile procedure without the use of $H_2$ gas, which hydrolyzes efficiently benzylic ether group under mild condition. [6].

Therefore, what is needed is new Metal-Organic Frameworks (MOFs) that can have a variety of metal-containing units.

What is needed is new Metal-Organic Frameworks (MOFs) that have various pore volumes.

What is needed is a method of removing benzyl ether without using hydrogen gas ($H_2$).

Furthermore, what is needed is new Metal-Organic Frameworks (MOFs) that contain new hexagonal mesoporous frameworks for the efficiently catalytic chemical fixation of $CO_2$.

Finally, what is needed is a method of synthesizing new Metal-Organic frameworks (MOFs).

The Metal-Organic Framework (MOF) and the method of synthesis disclosed in the present invention solve the above-described problems and objectives.

SUMMARY OF THE INVENTION

Accordingly, an object of the present invention is to provide a process for a multi-step synthesis of a Metal-Organic Framework that can adapt to different metal sites and therefore have different pore volumes that include:

(a) protecting of phenolic hydroxyl group using a benzylic ether (OBn) protection group through the reaction of hydroxy iodobenzoate and benzyl bromide (BnBr) for producing benzyloxy iodobenzoate compound;

(b) producing of ethyne bis(benzyloxybenzoate) compound by the Sonogashira cross-coupling method of benzyloxy iodobenzoate obtained in step (a);

(c) hydroxylating benzylic ether of bis(benzyloxybenzoate) compound obtained in step (b) by reacting with trimethylsilyl iodide (TMSI) for producing bis(hydroxybenzoate) compound;

(d) saponificating of bis(hydroxybenzoate) in a strong base solution for producing bis(hydroxybenzoic acid) compound;

(e) heating at elevated temperature liquid medium containing metal salt, bis(hydroxybenzoic acid) compound, a mixture of solvents in a sealed vial or an air-free tube under inert atmosphere for producing the as-synthesized Metal-Organic Framework (MOF);

(f) cooling liquid medium to room temperature, decanting the mother solution; and washing with anhydrous alcohol or anhydrous solvents for producing the solvent-exchanged Metal-Organic Framework (MOF).

(g) drying solvent-exchange Metal-Organic Framework (MOF) by vacuum under room temperature followed by heating at elevated temperature for producing the solvent-free Metal-Organic Framework (MOF).

Another object of the present invention is to provide a Metal-Organic Framework, which is a porous isostructural Metal-Organic Frameworks (MOFs), termed herein as M-VNU-93, wherein M comprises a metal ion (M=Mg, Ni, Co, Zn, Fe, Cu). M-VNU-93 exhibit selective $CO_2$ adsorption and efficiently catalytic activity for chemical fixation of $CO_2$ and epoxide in order to produce cyclic carbonate compounds Another object of the present invention is to provide a Metal-Organic Framework having the extended structure of MOF-74 and comprising bis(hydroxybenzoic acid) linking ligand.

Another object of the present invention is to provide a Metal-Organic Framework comprising bis(2-hydroxybenzoic acid) linking ligand, 4,4'-(ethyne-1,2-diyl)bis(2-hydroxybenzoic acid) linking ligand, and having a formula:

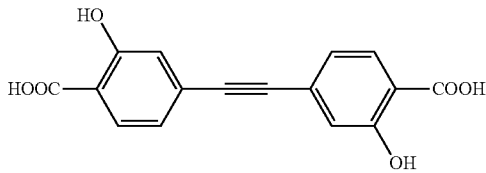

Another object of the present invention is to provide a Metal-Organic Framework comprising at least one divalent transition metal or alkaline earth metal such as magnesium, cobalt, nickel, zinc, copper, iron.

Another object of the present invention is to provide a Metal-Organic Framework comprising divalent transition metal or alkaline earth metal ion such as $Mg^{2+}$, $Co^{2+}$, $Ni^{2+}$, $Zn^{2+}$, $Cu^{2+}$, $Fe^{2+}$ These and other advantages of the present invention will no doubt become obvious to those of ordinary skill in the art after having read the following detailed description of the preferred embodiments, which are illustrated in the various drawing figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Figure 1:
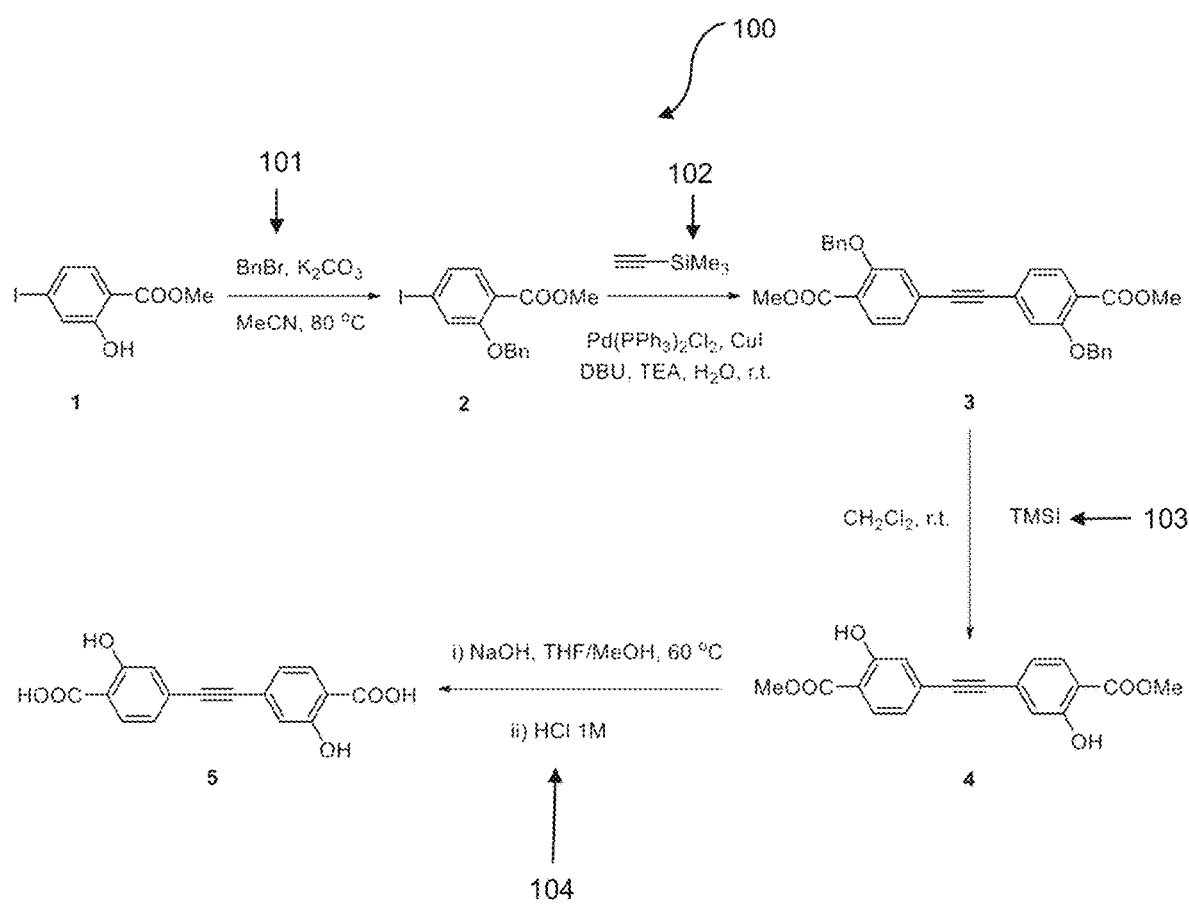
FIG. 1 shows the synthetic route to one of the linking ligands, i.e. 4,4'-(ethyne-1,2-diyl)bis(2-hydroxybenzoic acid) (EDHB), of the Metal-Organic Framework (MOF) M-VNU-93 in accordance with an exemplary embodiment of the present invention.

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, and components have not been described in detail so as not to unnecessarily obscure aspects of the present invention.

Disclosed in the present specification is a new "Metal-Organic Frameworks" (MOF) family named as M-VNU-93 that does not yet exist in the market or the laboratories. M-VNU-93 is a class of materials which is constructed by metal-containing units (secondary building units "SBUs") interconnected with an organic linker such as 4,4'-(ethyne-1,2-diyl)bis(2-hydroxybenzoic acid) (EDHB).[7]

In the beginning, the synthesis procedure of EDHB linker and the method of achieving the new class of metal organic frameworks named M-VNU-93 are disclosed. The pores structures of M-VNU-93, following by the powder X-ray diffraction patterns (PXRD), scanning electron microscopic (SEM) images and their porosities are described. The $CO_2$ adsorption properties of the new MOF (M-VNU-93) is disclosed via $CO_2$ isotherms at different temperatures. The catalytic performances in the formation of styrene carbonate via cycloaddition of $CO_2$ and styrene oxide catalyzed by M-VNU-93 are also provided.

In the end, the experiments and measurements for M-VNU-93 carried out in the laboratories are provided to support the M-VNU-93 series and their characteristics of the present invention are disclosed.

The terms "pores" described herein in the context of the Metal-Organic Framework are defined as open internal space confined in the frameworks. Pores are accessible for guest molecules when the MOFs are activated to remove the solvent molecules. The terms "linker" and "ligand" can be used interchangeably herein.

An "isostructural Metal-Organic Framework" is a family of MOFs with the same underlying topology and made by different metal ions with have an identical geometry of SBU; and/or expanded and functionalized organic linkers.

The procedure of benzylic ether hydrolysis disclosed herein containing the use of trimethylsilyl iodide (TMSI) in the presence of dichloromethane for a facile cleavage of benzylic ether protection group at room temperature for a couple of hours. The procedure is a selective deprotection method for the cleavage of benzylic ether groups among the other methyl ester groups.

Synthesis of M-VNU-93

A new Metal-Organic Framework (MOF) family, named as M-VNU-93, is comprised of an organic ligand and metal ions such as $Mg^{2+}$, $Zn^{2+}$, $Ni^{2+}$, $Co^{2+}$, $Fe^{2+}$, $Cu^{2+}$ FIG. 1 of the present disclosure discloses the synthesis of the organic ligand known as EDHB. FIG. 2 discloses the structures of the metal sites known as secondary building unit (SBU).

Now referring to FIG. 1, a multi-step chemical reaction 100 to synthesize a new organic ligand for M-VNU-93 is illustrated. The organic ligand, linking ligand, organic linker are referred to the same term to describe a molecule that binds other metal atoms to form a coordination complex. Linking ligand disclosed in the present invention include 4,4'-(ethyne-1,2-diyl)bis(2-hydroxybenzoic acid) (EDHB). In various embodiments of the present invention, multi-step chemical reaction 100 for synthesizing 4,4'-(ethyne-1,2-diyl)bis(2-hydroxybenzoic acid) (EDHB) is disclosed which includes a protection step 101 for protecting a hydroxyl group (—OH) in an alcohol compound, a cross-coupling step 102 of the result compound obtained in step 101, a cleavage step 103 of compound obtained in step 102, and a deprotection step 104 to obtain M-VNU-93.

More particularly, in protection step 101, a hydroxyl group (—OH) is protected by a protection reaction between a protection group and a functional group. In an exemplary implementation of protection step 101, the phenolic hydroxyl alcohol is protected or masked using a benzylic ether (OBn) protection group by performing the reaction of methyl hydroxy iodobenzoate and benzyl bromide (BnBr) to produce benzyloxy iodobenzoate compound. Benzyl bromide (BnBr) and potassium carbonate ($K_2CO_3$) are used as reagents and acetonitrile (MeCN) is used as a solvent in a temperature around 80° C. for 16 hours. Benzyl ether group (OBn) is attached to hydroxyl (OH) to form benzyloxy iodobenzoate that is inert to subsequent reaction steps 102-104.

Next in Sonogashira coupling reaction 102, Sonogashira palladium-catalyzed cross-coupling reaction is a reliable synthetic strategy in the formation of arylethynylene compounds. In general, the Sonogashira reaction is performed in the presence of relative amount of palladium-phosphine ligand complex as catalyst, copper(I) iodide salt as a co-catalyst, and amine in organic solvents. The original Sonogashira reaction was also required prior installation of (i) a trimethylsilylethynylene step of arylhalide compound, followed by (ii) a deprotection of silane to afford a terminal ethynylene before (iii) a cross-coupling reaction of to produce bisarylethynylenes. In this step 102 of this invention, a modification Sonogashira reaction is performed which proceeds in the one-pot generation of bisarylethynylenes between the compounds obtained in protection step 101 above, which is respected for efficiently synthetic procedures. In various implements of cross-coupling step 102, the Sonogashira cross-coupling is conducted with the aid of an amidine base 1,8-diazabicyclo[5.4.0]undec-7-ene (DBU) and the presence of substoichiometric amounts of water, in addition to $Pd^{2+}$ catalyst, CuI, trimethylsilylethynylene and triethylamine (TEA).[8]

In cleavage or hydroxylation step 103, hydroxylating of benzylic ether (OBn) in bis(benzyloxybenzoate) compound is performed. In other words, hydroxylation step 103 introduces the hydroxyl (—OH) group into the bis(benzyloxybenzoate) to obtain bis(hydroxybenzoate). The oxygen-carbon bond of benzylic ether (OBn) is replaced by a oxygen-hydrogen bond of the hydroxyl (—OH) in the bis(benzyloxybenzoate) compound in dichloromethane ($CH_2Cl_2$) solvent using an organosilicon reactant such as trimethylsilyl iodide (TMSI).

In deprotection step 104 of multistep synthesis 100, a base such as NaOH is added in a solution of the bis(hydroxybenzoate) compound in tetrahydrofuran/methanol (THF/MeOH) solution. The reaction mixture is stirred and refluxed at 60° C. for 24 hours. Then, the mixture is acidified with hydrochloride acid (HCl) (1 mole) to obtain 4,4'-(ethyne-1,2-diyl)bis(2-hydroxybenzoic acid) (EDHB) linker.

Figures 2A, 2B:
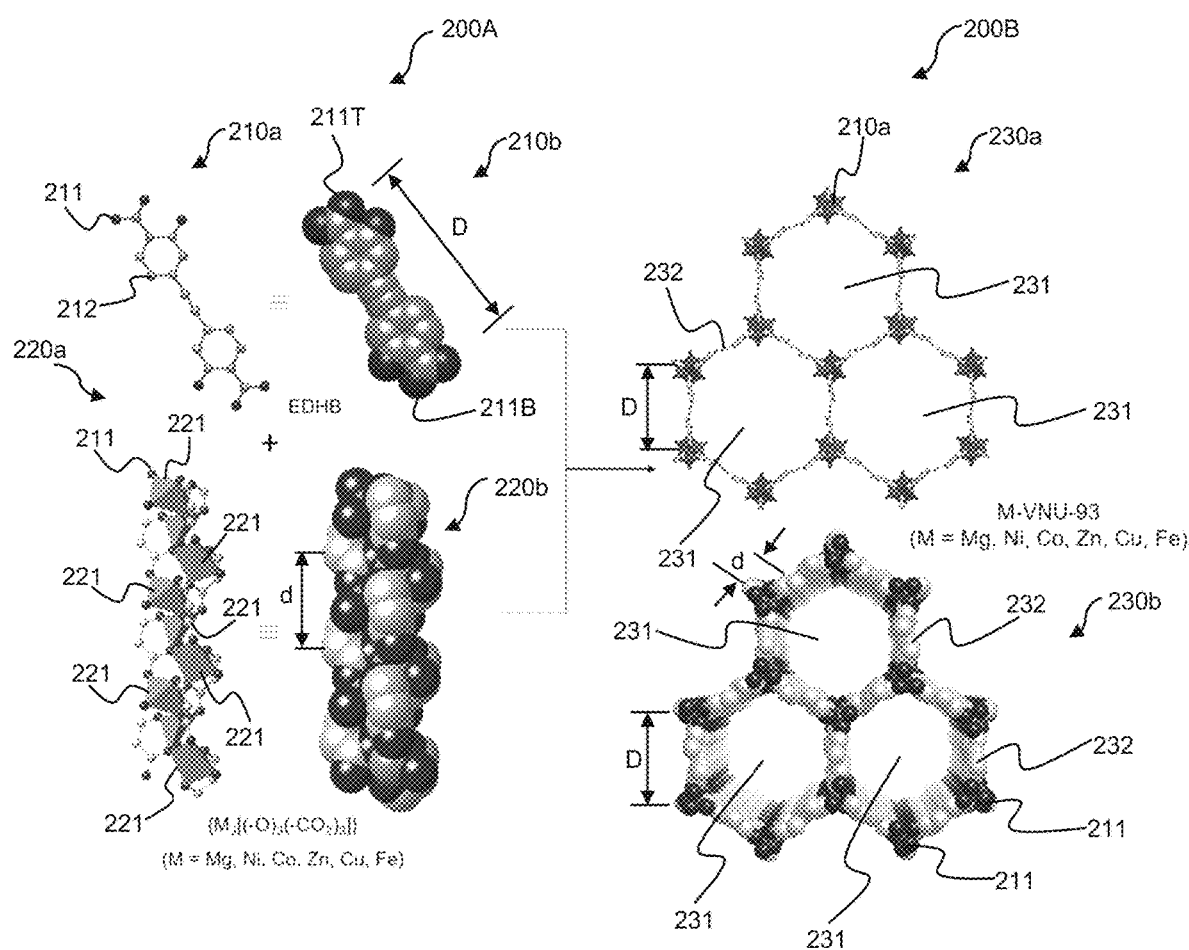
FIG. 2A shows two-dimension (2D) and three-dimension (3D) reaction between the linking ligand EDHB and metal-oxo clusters $\{M_3[(-O)_3(-CO_2)_3]\}\infty$ in accordance with an exemplary embodiment of the present invention.
FIG. 2B shows two-dimension (2D) and three-dimension (3D) structure of M-VNU-93 in accordance with an exemplary embodiment of the present invention.

Now referring to FIG. 2A and FIG. 2B, two-dimensional and 3-dimensional (3D) crystal structure M-VNU-93 series as a result from the reaction between a 4,4'-(ethyne-1,2-diyl) bis(2-hydroxybenzoic acid)) (EDHB) linker and a metal oxide secondary building unit (SBU) are showed.

In FIG. 200A, a formula 210a is a two-dimensional (2D) representation of a linking ligand named as EDHB. A formula 210b is a three-dimensional (3D) representation of the same linking ligand used in a reaction 200A. Linking ligand 210a and 210b include oxygen 211 atoms and carbon atoms 212. Hydrogen atoms are not shown for clarity purpose and to avoid confusion. Linking ligand 210a and 210b have a long axis D between a top oxygen atom 211T and a bottom oxygen atom 211B. A short axis d is the distance of metal open sites 221. A formula 220a is a two-dimensional (2D) representation of oxide metal secondary building unit (SBU). A formula 220b is a three-dimensional (3D) representation of the same oxide metal SBU used in a reaction 200A. Metal oxide SBU 220a, 220b are open metal sites having an M-O—C core structure with the general formula of $\{M_3[(—O)_3(—CO_2)_3]\}\infty$ where M includes Mg, Ni, Co, Zn, Cu, and Fe. In reaction 200A between linking ligand 210a and metal oxide secondary building unit (SBU) 220a, M-VNU-93 230a, 230b is formed by the precise linkage of EDHB linker 210a, 210b with an extended framework composed of channels along the direction of the short axis d that are isolated by walls formed by the aforementioned packing of EDHB linker 210a, 210b, a construct that forbids interpenetration regardless of the length of organic linker.

Referring now to FIG. 200B, a two-dimension (2D) structure 230a of M-VNU-93 illustrates pores 231 and short axis d. In a three-dimensional (3D) structure 230b of M-VNU-93, long axis D of linking ligand 210a, 210b determines the diameter of M-VNU-93 230a, 230b. Again, EDHB linker 210a, 210b is connected with a metal oxide SBU 220a, 220b to achieve the three-dimensional M-VNU-93 structure with one-dimensional hexagonal channels. M-VNU-93 230a, 230b disclosed in FIG. 1 and FIG. 2 above comprises the general structure $M_2$(EDHB) (M=$Mg^{2+}$, $Zn^{2+}$, $Ni^{2+}$, $Co^{2+}$, $Fe^{2+}$, $Cu^{2+}$ where EDHB linker 210a, 210b is 4,4'-(ethyne-1,2-diyl)bis(2-hydroxybenzoic acid)). In the structure of M-VNU-93 230a, 230b, infinite rod-shaped metal oxide building units (SBU) 220a, 220b with a formula of $\{M_3[(—O)_3(—CO_2)_3]\}\infty$ are joined by organic linker 210a, 210b comprising the carboxylic and the ortho-positioned hydroxyl functionalities, original dioxidoterephthalate, to result in the three-dimensional structure with one-dimensional hexagonal channel of 24 Å. It will be appreciated in the present invention that six M-VNU-93 materials are mesoporous materials with the diameter of the hexagonal channel of 24 Å.

M-VNU-93 230a, 230b described in the present disclosure contains pores 231 as accessible aperture, in particular micropores and/or mesopores. Micropores are defined as pores having a diameter of 2 nm or less, and mesopores are defined by a diameter in the range from 2 nm to 50 nm.

Detailed crystallographic information for M-VNU-93 230a, 230b series including unit cell parameter, pore aperture dimension, density, and void volume of the structural model is listed in Table 1. Obviously, the lattice parameters, unit cell volumes, densities and void columes for each M-VNU-93 compound were different due to the variation of the ionic radii of divalent cations with 5-connected geometry. The pore aperture metrics of the channels were found in the range diameter of 23.6-24.5 Å, imply of mesoporous nature for M-VNU-93. The largest and smallest unit cell volume was found to be 10529 Å$^3$ for Mg-VNU-93 and 9382 Å$^3$ for Ni-VNU-93, respectively. For comparison, the pore apertures of M-VNU-93 are larger than IRMOF-74-II (19.5 Å) and smaller than IRMOF-74-III (27.3 Å), respectively.[1] The density of and void volumes were also calculated with the trend Mg<Fe<Cu<Co<Zn<Ni and Zn<Cu<Ni<Co<Fe<Mg, respectively.

TABLE 1

| Compound | Formula | a (Å) | c (Å) | Unit cell volume (Å$^3$) | Pore aperture metrics (Å) | Density (g · cm$^{-3}$) | Void volume (%) |
|---|---|---|---|---|---|---|---|
| Mg-VNU-93 | Mg$_2$C$_{16}$H$_6$O$_6$ | 42.0211 | 6.4160 | 10529.331 | 23.6 | 0.5377 | 74.6 |
| Co-VNU-93 | Co$_2$C$_{16}$H$_6$O$_6$ | 40.7877 | 6.1185 | 9672.338 | 24.8 | 0.6924 | 72.0 |
| Ni-VNU-93 | Ni$_2$C$_{16}$H$_6$O$_6$ | 40.7446 | 5.9689 | 9382.172 | 23.6 | 0.7131 | 71.8 |
| Zn-VNU-93 | Zn$_2$C$_{16}$H$_6$O$_6$ | 41.1456 | 5.5642 | 9685.613 | 22.6 | 0.7113 | 70.2 |
| Fe-VNU-93 | Fe$_2$C$_{16}$H$_6$O$_6$ | 41.1500 | 6.3129 | 10030.105 | 24.5 | 0.6585 | 72.6 |
| Cu-VNU-93 | Cu$_2$C$_{16}$H$_6$O$_6$ | 41.1539 | 5.7738 | 9937.747 | 24.5 | 0.6878 | 71.0 | metal atoms 221. In this way, the aperture of pore 231 of M-VNU-93 230a, 230b can be controlled on the angstrom level through the increase in long axis D or the number of atoms in EDHB linker 210a, 210b. The resulting product is FIG. 3-FIG. 8 illustrate the comparisons of experimental PXRD patterns of as-synthesized M-VNU-93 series with the simulated M-VNU-93 series diffraction patterns. It was proved that M-VNU-93 series 230a, 230b are highly crystalline, as demonstrated by their sharp X-ray diffraction peaks observed in the following FIGS.

Figure 3:
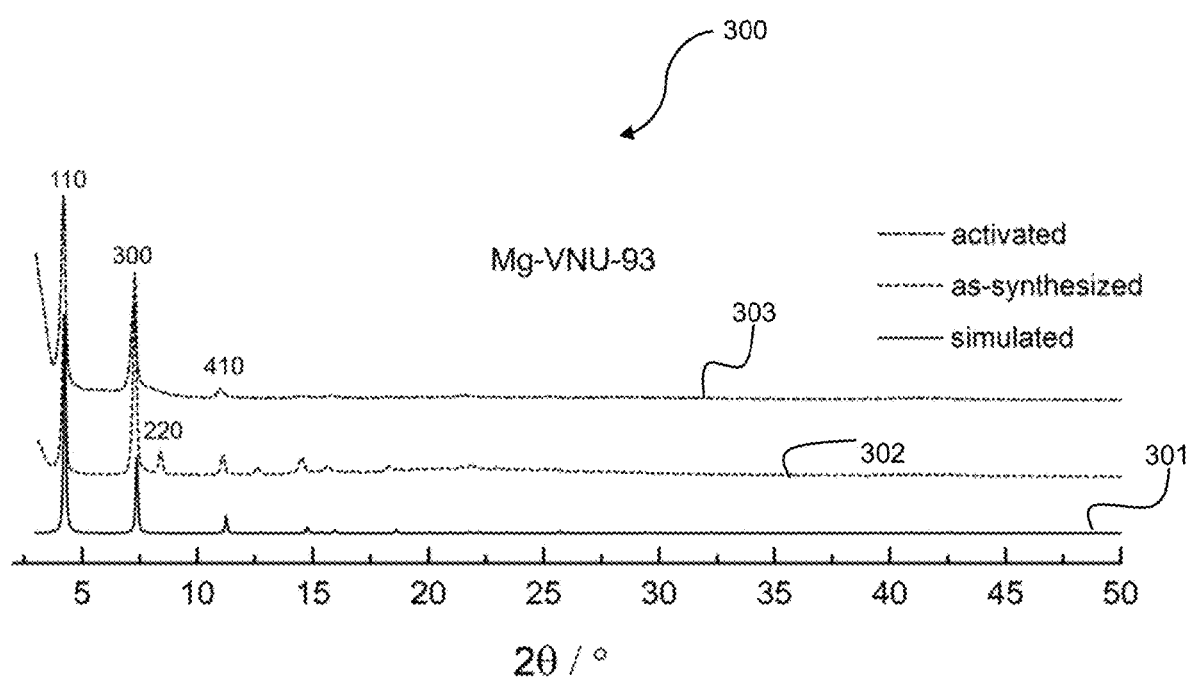
FIG. 3 shows the comparison of experimental PXRD pattern of the as-synthesized Mg-VNU-93 with the simulated Mg-VNU-93 diffraction pattern in accordance with an aspect of the present invention.

Referring to FIG. 3, a graph 300 illustrates X-ray diffraction patterns (PXRD) of Mg-VNU-93 in the M-VNU-93 series where Mg is magnesium (Mg). In graph 300, the vertical axis is relative intensity in an arbitrary unit (a.u.). An arbitrary unit is a relative unit of intensity measurement that shows the ratio amount of intensity to a predetermined reference measurement. The horizontal axis in graph 300 indicates the position of the detector in degrees. The PXRD measurement to determine the crystalline structure of the chemical composition is well known in the art and needs not to be described in details here. In graph 300, there are three plots: a plot 301 indicates the simulated diffraction pattern, a plot 302 is the as-synthesized diffraction pattern, and a plot 303 is an activated diffraction pattern of Mg-VNU-93. These three plots 301, 302, and 303 show that Mg-VNU-93 is a highly crystalline material because they are expressed by sharp peaks. The position of the peaks in three plots 301, 302, and 303 are in good agreement, confirming that the predicted Mg-VNU-93 structure was successfully synthesized in large amount and desolvated or activated without degradation of the structure.

Figure 4:
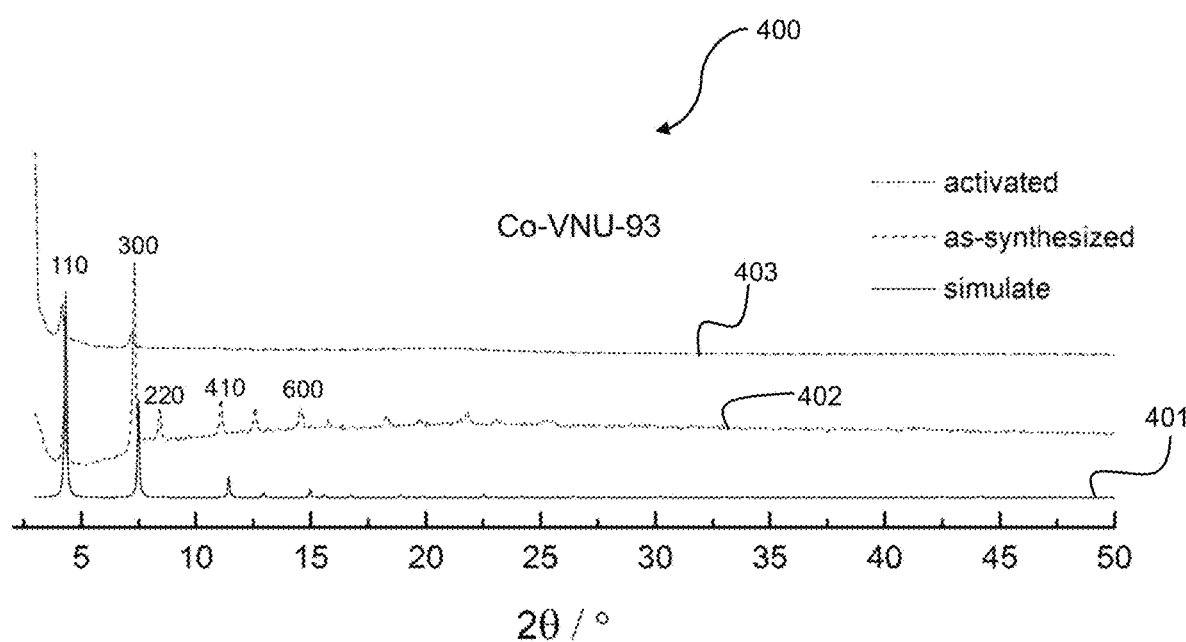
FIG. 4 shows the comparison of experimental PXRD pattern of the as-synthesized Co-VNU-93 with the simulated Co-VNU-93 diffraction pattern in accordance with an aspect of the present invention.

Referring to FIG. 4, a graph 400 illustrates X-ray diffraction patterns (PXRD) of Co-VNU-93 in the M-VNU-93 series where Co is the abbreviation of Cobalt (Co). In graph 400, the vertical axis is relative intensity in arbitrary unit (a.u.). An arbitrary unit is a relative unit of intensity measurement that shows the ratio amount of intensity to a predetermined reference measurement. The horizontal axis in graph 400 indicates the position of the detector in degrees. In graph 400, there are three plots: a plot 401 indicates the simulated diffraction pattern, a plot 402 is the as-synthesized diffraction pattern, and a plot 403 is an activated diffraction pattern of Co-VNU-93. These three plots 401, 402, and 403 show that Co-VNU-93 is also a highly crystalline material because they are expressed by sharp peaks. The position of the peaks in three plots 401, 402, and 403 are in good agreement, confirming that the predicted Co-VNU-93 structure was successfully synthesized in large amount and desolvated or activated without degradation of the structure.

Figure 5:
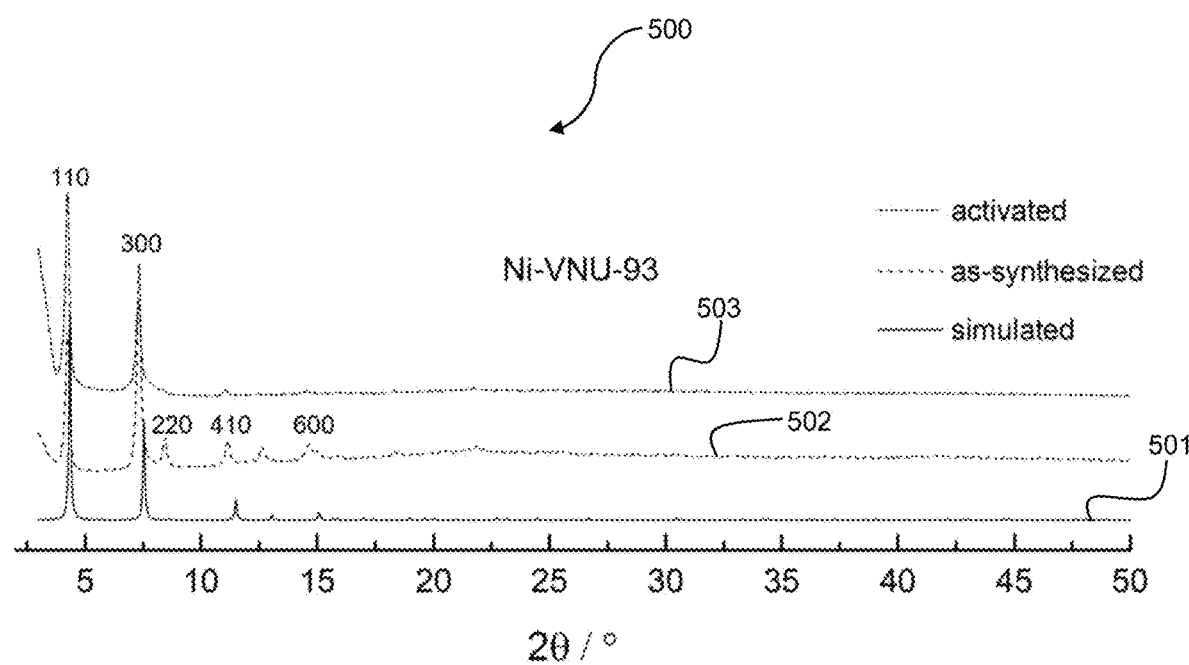
FIG. 5 shows the comparison of experimental PXRD pattern of the as-synthesized Ni-VNU-93 with the simulated Ni-VNU-93 diffraction pattern in accordance with an aspect of the present invention.

Referring to FIG. 5, a graph 500 illustrates X-ray diffraction patterns (PXRD) of Ni-VNU-93 in the M-VNU-93 series where Ni is the abbreviation of nickel (Ni). In graph 500, the vertical axis is relative intensity in an arbitrary unit (a.u.). An arbitrary unit is a relative unit of intensity measurement that shows the ratio amount of intensity to a predetermined reference measurement. The horizontal axis in graph 500 indicates the position of the detector in degrees. In graph 500, there are three plots: a plot 501 indicates the simulated diffraction pattern, a plot 502 is the as-synthesized diffraction pattern, and a plot 503 is an activated diffraction pattern of Ni-VNU-93. These three plots 501, 502, and 503 show that Ni-VNU-93 is also a highly crystalline material because they are expressed by sharp peaks. The position of the peaks in three plots 501, 502, and 503 are in good agreement, confirming that the predicted Ni-VNU-93 structure was successfully synthesized in large amount and desolvated or activated without degradation of the structure.

Figure 6:
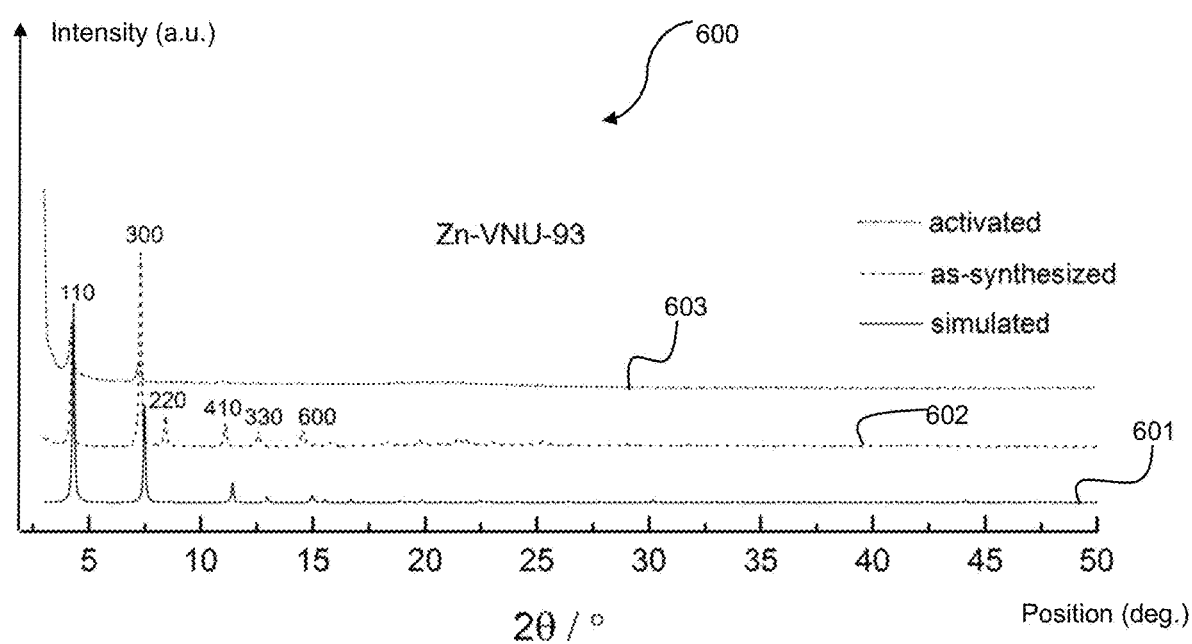
FIG. 6 shows the comparison of experimental PXRD pattern of the as-synthesized Cu-VNU-93 with the simulated Cu-VNU-93 diffraction pattern in accordance with an aspect of the present invention.

Referring to FIG. 6, a graph 600 illustrates X-ray diffraction patterns (PXRD) of Zn-VNU-93 in the M-VNU-93 series where Zn is the abbreviation of Zinc (Zn). In graph 600, the vertical axis is relative intensity in an arbitrary unit (a.u.). An arbitrary unit is a relative unit of intensity measurement that shows the ratio amount of intensity to a predetermined reference measurement. The horizontal axis in graph 600 indicates the position of the detector in degrees. In graph 600, there are three plots: a plot 601 indicates the simulated diffraction pattern, a plot 602 is the as-synthesized diffraction pattern, and a plot 603 is an activated diffraction pattern of Zn-VNU-93. These three plots 601, 602, and 603 show that Zn-VNU-93 is also a highly crystalline material because they are expressed by sharp peaks. The position of the peaks in three plots 601, 602, and 603 are in good agreement, confirming that the predicted Zn-VNU-93 structure was successfully synthesized in large amount and desolvated or activated without degradation of the structure.

Figure 7:
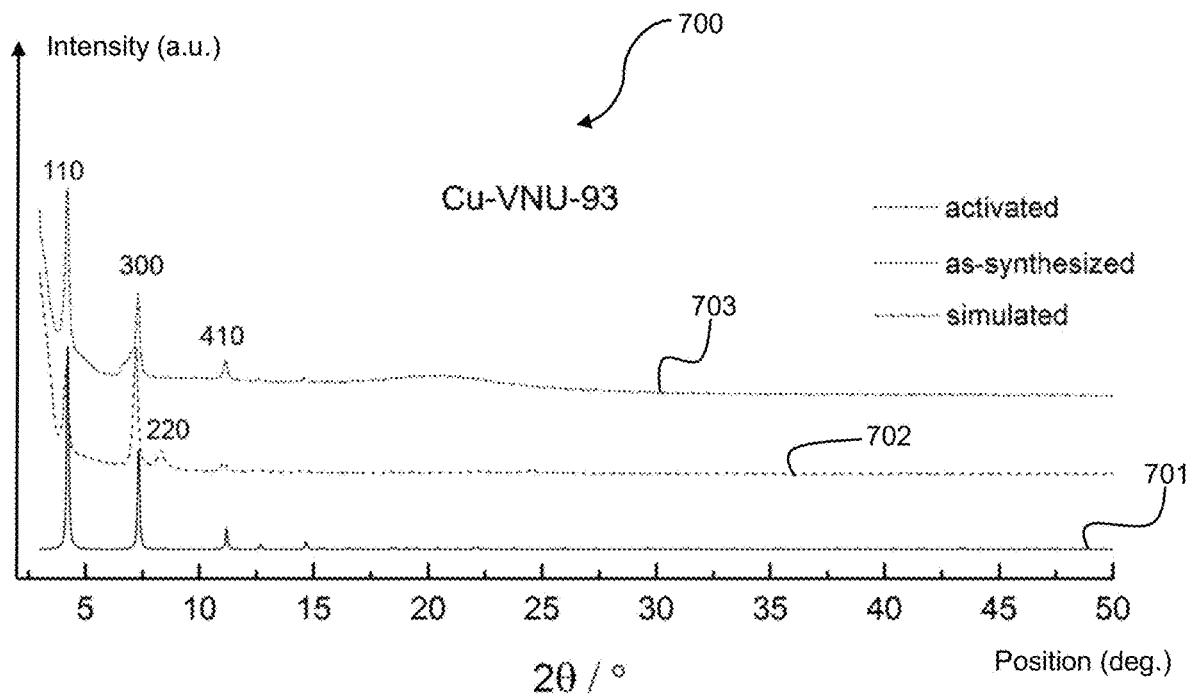
FIG. 7 shows the comparison of experimental PXRD pattern of the as-synthesized Cu-VNU-93 with the simulated Cu-VNU-93 diffraction pattern in accordance with an aspect of the present invention.

Referring to FIG. 7, a graph 700 illustrates X-ray diffraction patterns (PXRD) of Copper-VNU-93 in the M-VNU-93 series where Cu is the abbreviation of copper (Cu). In graph 700, the vertical axis is relative intensity in an arbitrary unit (a.u.). An arbitrary unit is a relative unit of intensity measurement that shows the ratio amount of intensity to a predetermined reference measurement. The horizontal axis in graph 700 indicates the position of the detector in degrees. In graph 700, there are three plots: a plot 701 indicates the simulated diffraction pattern, a plot 702 is the as-synthesized diffraction pattern, and a plot 703 is an activated diffraction pattern of Cu-VNU-93. These three plots 701, 702, and 703 show that Cu-VNU-93 is also a highly crystalline material because they are expressed by sharp peaks. The position of the peaks in three plots 701, 702, and 703 are in good agreement, confirming that the predicted Cu-VNU-93 structure was successfully synthesized in large amount and desolvated or activated without degradation of the structure.

Figure 8:
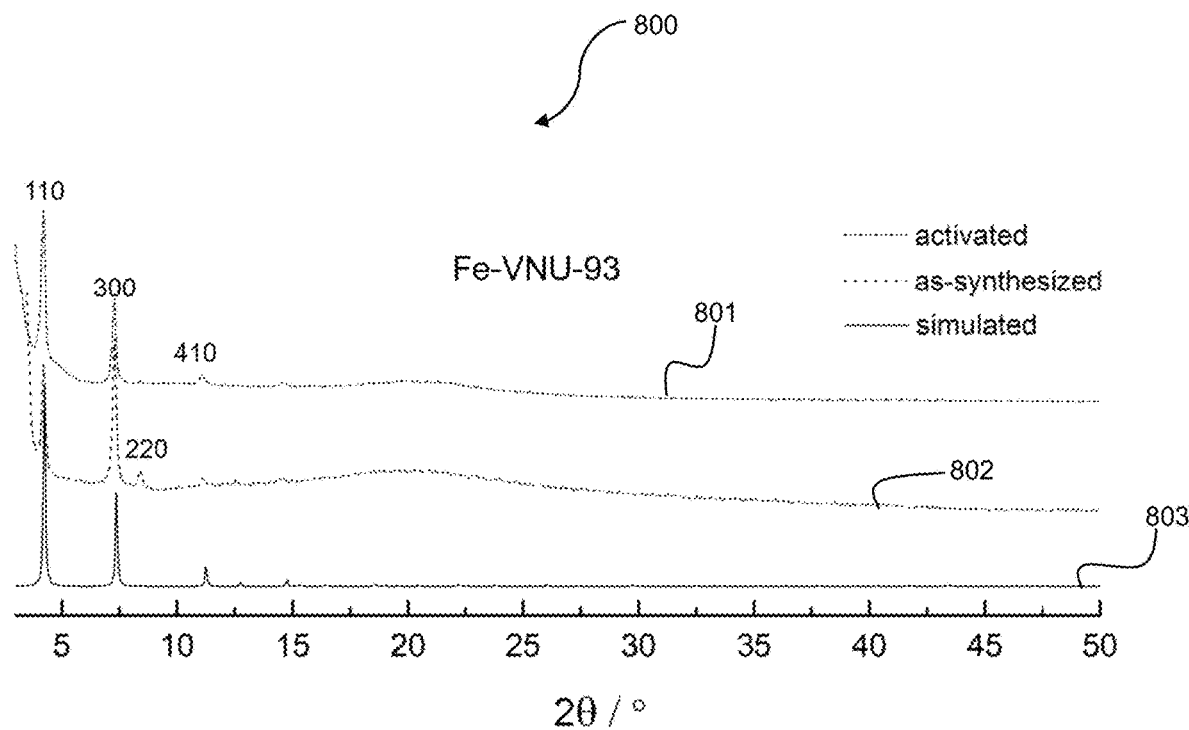
FIG. 8 shows the comparison of experimental PXRD pattern of the as-synthesized Fe-VNU-93 with the simulated Fe-VNU-93 diffraction pattern in accordance with an aspect of the present invention.

Referring to FIG. 8, a graph 800 illustrates X-ray diffraction patterns (PXRD) of Fe-VNU-93 in the M-VNU-93 series where Fe is the abbreviation of iron (Fe). In graph 800, the vertical axis is relative intensity in an arbitrary unit (a.u.). An arbitrary unit is a relative unit of intensity measurement that shows the ratio amount of intensity to a predetermined reference measurement. The horizontal axis in graph 800 indicates the position of the detector in degrees. In graph 800, there are three plots: a plot 801 indicates the simulated diffraction pattern, a plot 802 is the as-synthesized diffraction pattern, and a plot 803 is an activated diffraction pattern of Fe-VNU-93. These three plots 801, 802, and 803 show that Fe-VNU-93 is also a highly crystalline material because they are expressed by sharp peaks. The position of the peaks in three plots 801, 802, and 803 are in good agreement, confirming that the predicted Fe-VNU-93 structure was successfully synthesized in large amount and desolvated or activated without degradation of the structure.

Next referring to FIG. 9-FIG. 14, FIG. 9-FIG. 14 illustrate the images of M-VNU-93 series captured by the scanning electron microscopic (SEM). Scanning electron microscopic (SEM) scans a focused electron beam over a surface of each M-VNU-93 to create an image. The electrons in the beam interact with the sample, producing various signals that can be used to obtain information about the surface topography and composition. The phase purity of each M-VNU-93 is confirmed by their singular crystal morphology as observed in the scanning electron microscopic (SEM) images.

Figure 9:
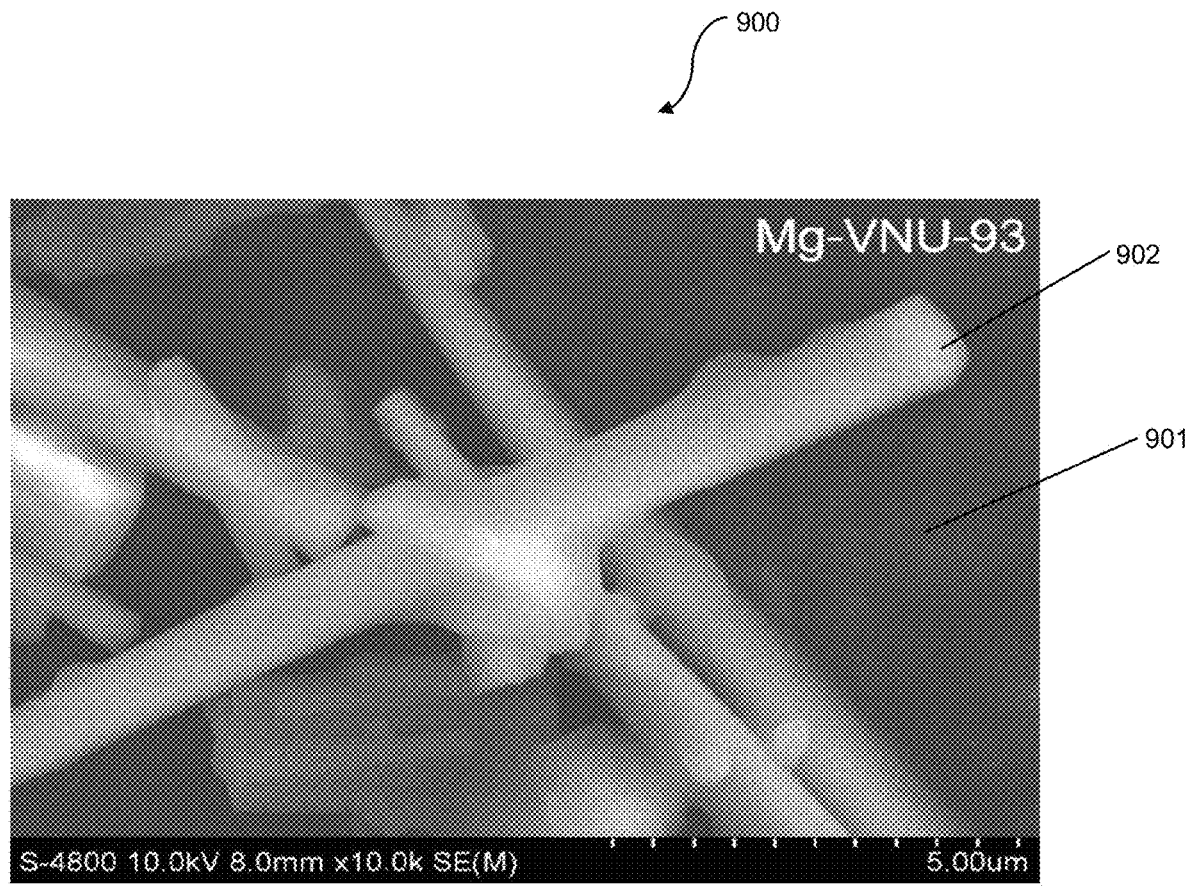
FIG. 9 is the Scanning Electron Microscopic (SEM) image which shows the single-phase morphology characteristics of Mg-VNU-93 in accordance with an aspect of the present invention.

Referring now to FIG. 9, an image 900 shows an SEM image of Mg-VNU-93. Image 900 is obtained using a Hitachi 4800 scanning electron microscope. The electron acceleration voltage is 10 k volts, the working distance between the objective lens and Mg-VNU-93 sample is 8.0 mm, and the magnification is 10,000 times. Image 900 shows a crystal structure 902 in a dark void background 901. This means that Mg-VNU-93 is highly crystalline and uniform as consistently shown by peaks in FIG. 3.

Figure 10:
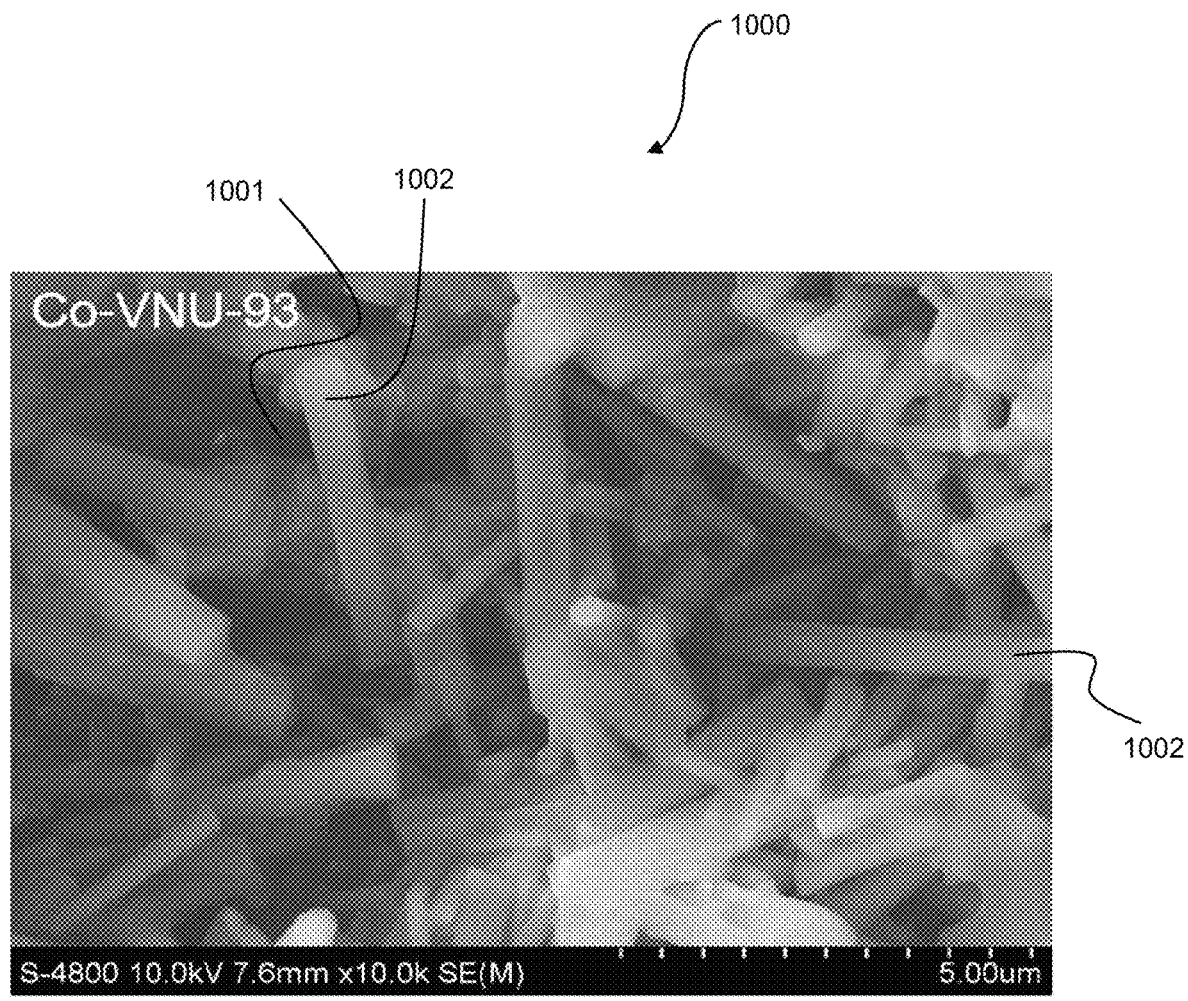
FIG. 10 is the Scanning Electron Microscopic (SEM) image showing single-phase morphology of Co-VNU-93 in accordance with an aspect of the present invention.

Referring now to FIG. 10, an image 1000 shows an SEM image of Co-VNU-93. Image 1000 is obtained using the Hitachi 4800 scanning electron microscope. The electron acceleration voltage is 10 k volts, the working distance between the objective lens and Co-VNU-93 sample is 7.6 mm, and the magnification is 10,000 times. Image 1000 shows mostly crystal structures 1002 in a dark void background 1001. This means that Co-VNU-93 is highly crystalline and uniform as consistently shown by peaks in FIG. 4.

Figure 11:
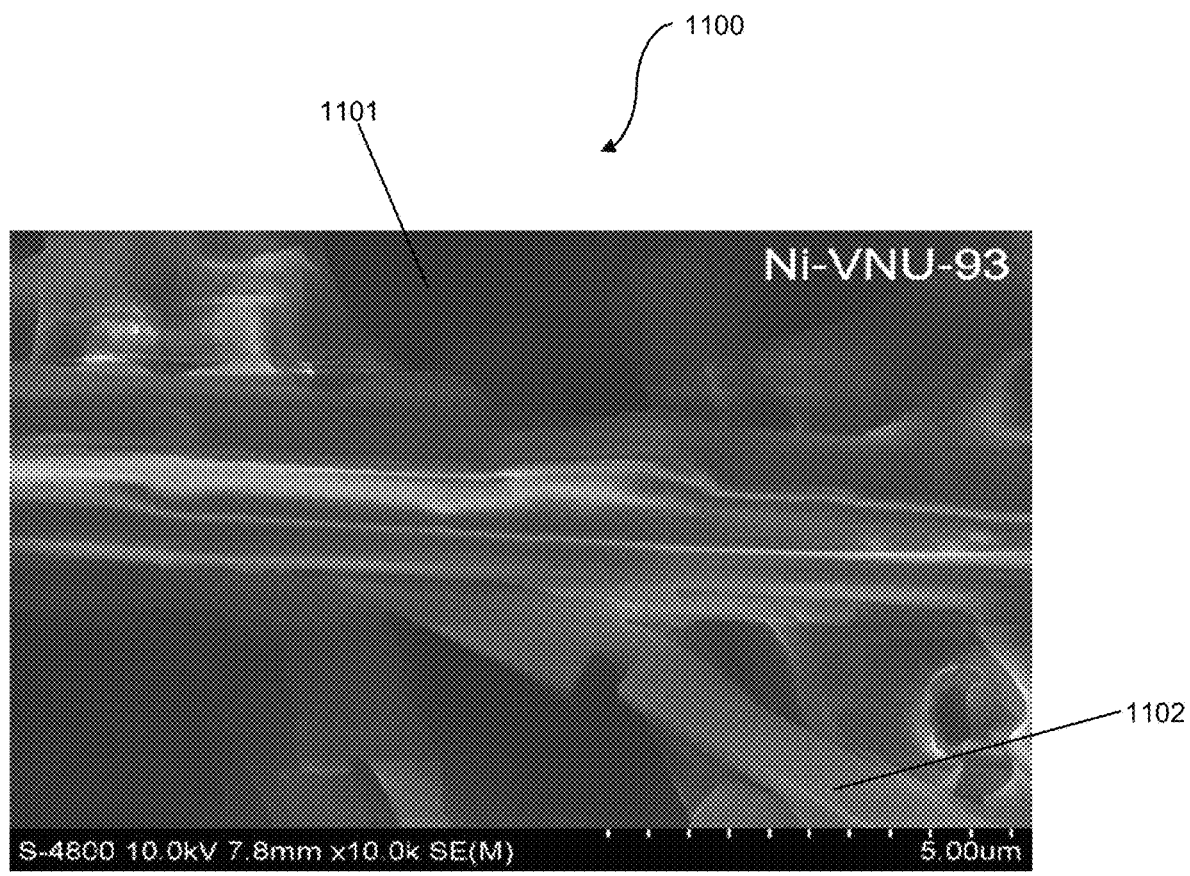
FIG. 11 is the Scanning Electron Microscopic (SEM) image showed single-phase morphology of Ni-VNU-93 in accordance with an aspect of the present invention.

Referring next to FIG. 11, an image 1100 shows an SEM image of Ni-VNU-93. Image 1100 is obtained using the Hitachi 4800 scanning electron microscope. The electron acceleration voltage is 10 k volts, the working distance between the objective lens and Co-VNU-93 sample is 7.6 mm, and the magnification is 10,000 times. Image 1100 shows mostly crystal structures 1102 in a dark void background 1101. This means that Ni-VNU-93 is highly crystalline and uniform as consistently shown by peaks in FIG. 5.

Figure 12:
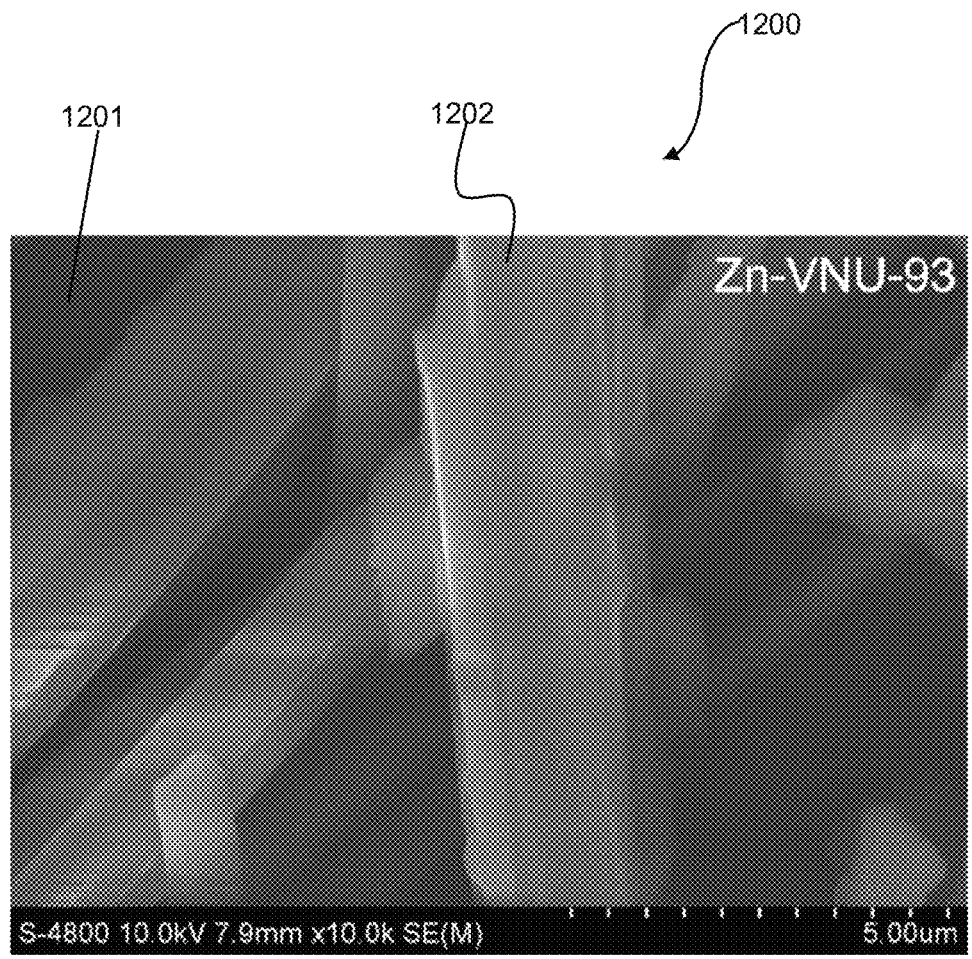
FIG. 12 is the Scanning Electron Microscopic (SEM) image showed single-phase morphology of Zn-VNU-93 in accordance with an aspect of the present invention.

Referring now to FIG. 12, an image 1200 shows an SEM image of Zn-VNU-93. Image 1200 is obtained using the Hitachi 4800 scanning electron microscope. The electron acceleration voltage is 10 k volts, the working distance between the objective lens and Zn-VNU-93 sample is 7.9 mm, and the magnification is 10,000 times. Image 1200 shows a crystal structure 1202 in a dark void background 1201. This means that Zn-VNU-93 is highly crystalline and uniform as consistently shown by peaks in FIG. 6.

Figure 13:
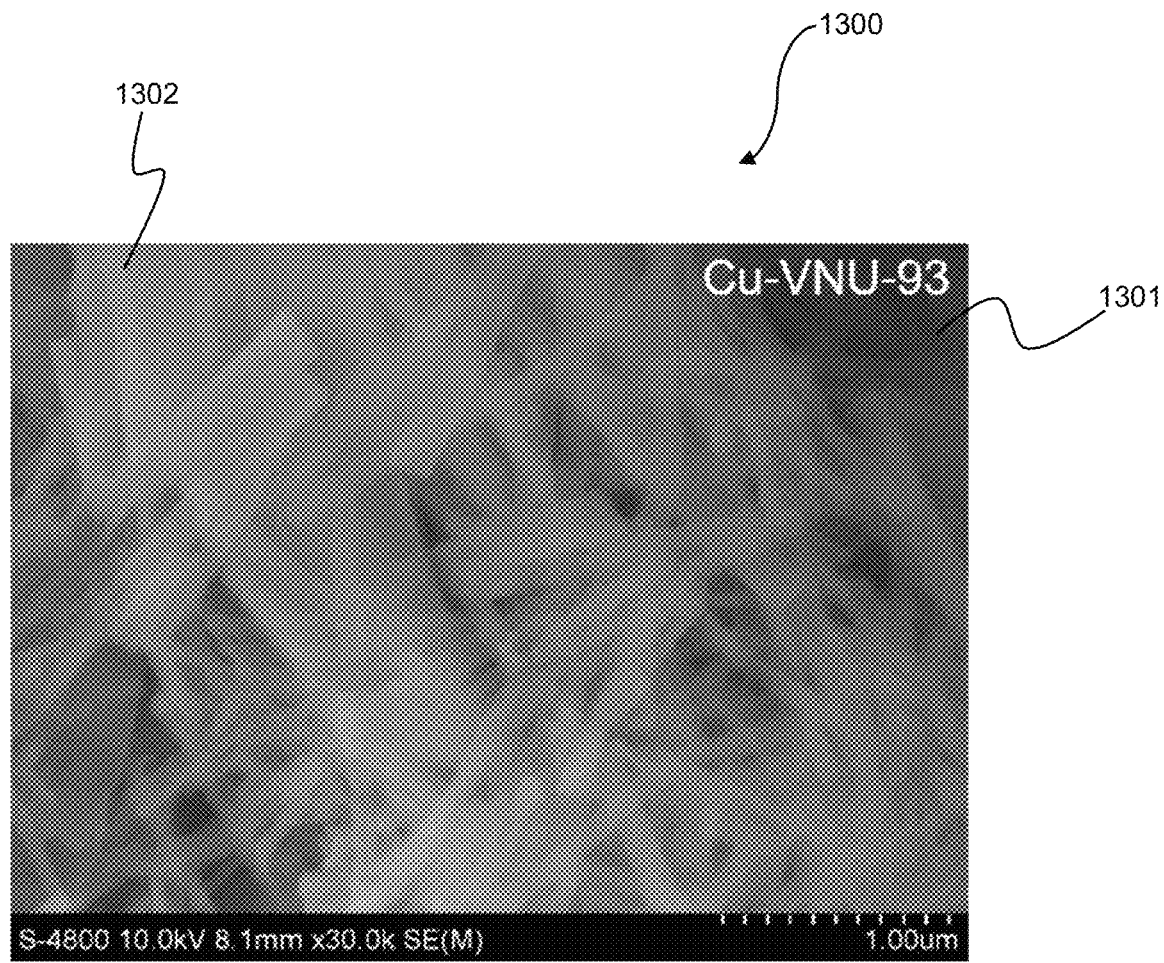
FIG. 13 is the Scanning Electron Microscopic (SEM) image showing single-phase morphology of Cu-VNU-93 in accordance with an aspect of the present invention.

Referring now to FIG. 13, an image 1300 shows an SEM image of Cu-VNU-93. Image 1300 is obtained using the Hitachi 4800 scanning electron microscope. The electron acceleration voltage is 10 k volts, the working distance between the objective lens and Cu-VNU-93 sample is 8.1 mm, and the magnification is 10,000 times. Image 1300 shows mostly crystal structures 1302 in a dark void background 1301. This means that Cu-VNU-93 is highly crystalline and uniform as consistently shown by peaks in FIG. 7.

Figure 14:
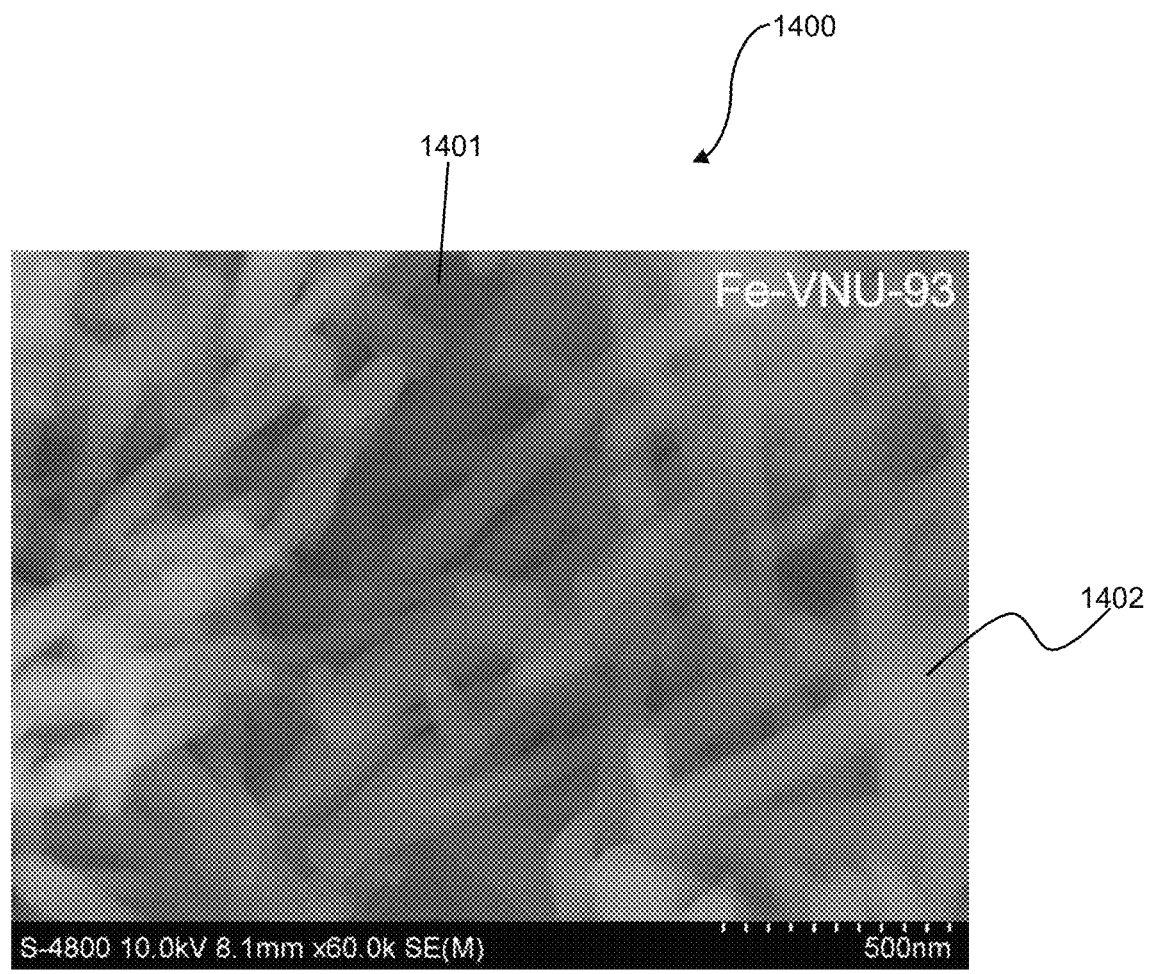
FIG. 14 is the Scanning Electron Microscopic (SEM) image showing single-phase morphology of Fe-VNU-93 in accordance with an aspect of the present invention.

Referring next to FIG. 14, an image 1400 shows an SEM image of Fe-VNU-93. Image 1400 is obtained using the Hitachi 4800 scanning electron microscope. The electron acceleration voltage is 10 k volts, the working distance between the objective lens and Fe-VNU-93 sample is 8.1 mm, and the magnification is 60,000 times. Image 1400 shows densely crystal structures 1402 in a very limited dark void background 1401. This means that Fe-VNU-93 is highly crystalline and uniform as consistently shown by peaks in FIG. 8.

Figure 15:
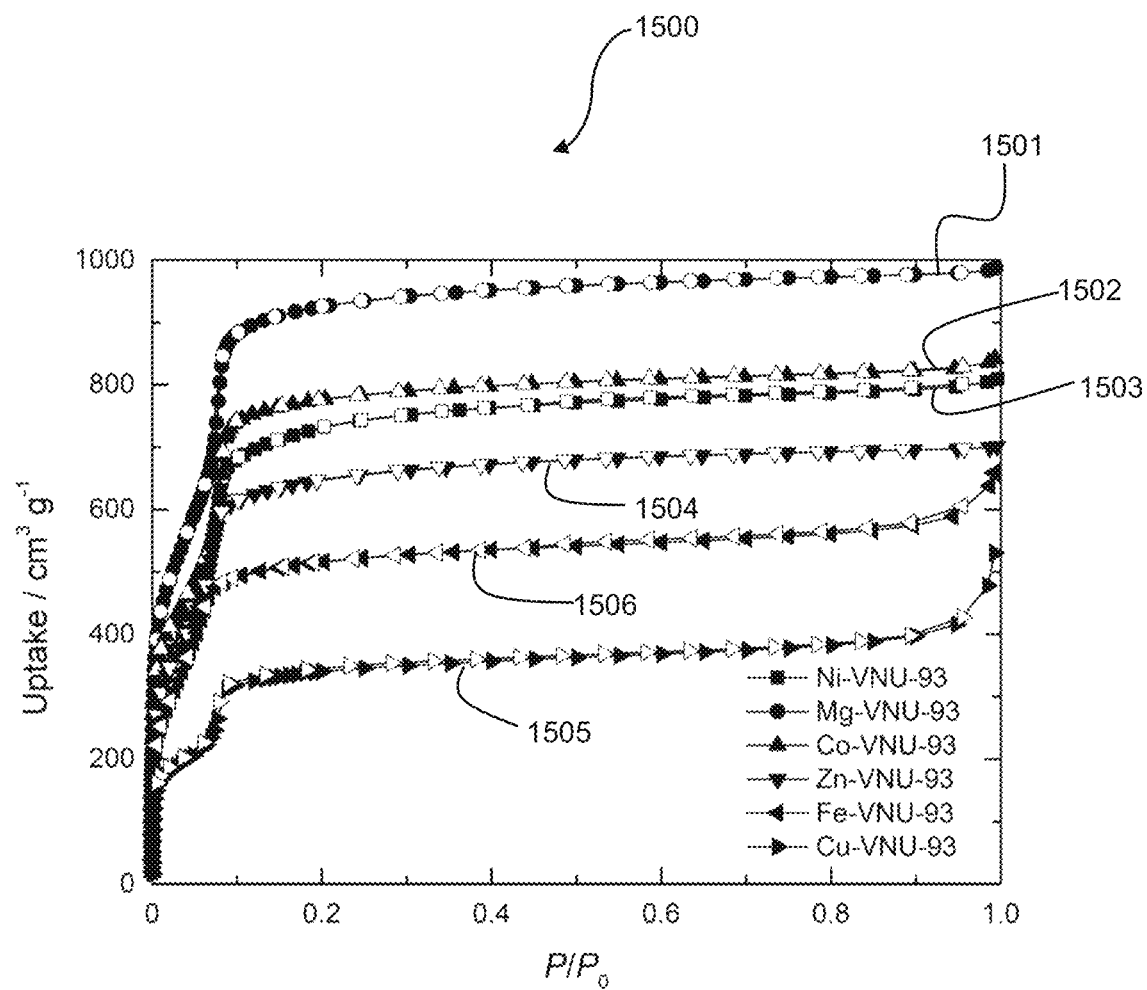
FIG. 15 are graphs of the $N_2$ isotherms for M-VNU-93 series at 77 K and relative pressure at $P/P_0$ in accordance with an aspect of the present invention.

FIG. 15 shows the $N_2$ isotherms adsorption/desorption curves 1500 for the M-VNU-93 series at 77 K. Adsorption is the sticking of gas molecules onto the surface of a solid, while desorption is the removal of gas molecules from the surface of M-VNU-93. An adsorption isotherm is obtained by measuring the amount of gas adsorbed across a wide range of relative pressures at a constant temperature, typically liquid nitrogen ($N_2$ at 77 K) is used as the adsorbate. Conversely, desorption isotherms are achieved by measuring gas removed as the relative pressure is reduced. In curves 1500, the vertical axis is the amount of gas molecules adsorbed or desorped (uptake) in $cm^3/g$ while the horizontal axis is relative pressure $P/P_0$. A graph 1501 represents the adsorption and desorption of Mg-VNU-93. A graph 1502 represents the adsorption and desorption of Co-VNU-93. A graph 1503 represents the adsorption and desorption of Ni-VNU-93. A graph 1504 represents the adsorption and desorption of Zn-VNU-93. A graph 1506 represents the adsorption and desorption of Cu-VNU-93. A graph 1506 represents the adsorption and desorption of Fe-VNU-93. Filled and open symbols in graphs 1501-1506 represent adsorption and desorption branches, respectively. The connecting curve is presented as a visual guide.

Continuing with FIG. 15, all graphs 1501-1506 show that M-VNU-93 series are type IV solids whose pores are typically mesoporous with the exposed surface residing almost exclusively inside the micropores, which once filled with adsorbate such as $N_2$, leaving little or no external surface for further adsorption. $N_2$ sorption measurements at 77 K were performed on the activated or desolvated M-VNU-93 to evaluate their porosity and architectural stability after activation. Accordingly, the resulting $N_2$ isotherms graphs 1501-1506 reveal a steep increase profile at $P/P_0=0.05-0.07$, be classified as type-IV, and indicative of mesoporous materials. Accordingly, Brunauer-Emmett-Teller (BET)/Langmuir surface areas are also calculated and found to be 4052/4232 $m^2 g^{-1}$ for Mg-VNU-93, 3246/3582 $m^2 g^{-1}$ for Co-VNU-93, 3252/3473 $m^2 g^{-1}$ for Ni-VNU-93, 2729/3028 $m^2 g^{-1}$, 2125/1670 $m^2 g^{-1}$ for Cu-VNU-93, and 3477/2424 $m^2 g^{-1}$ for Fe-VNU-93 (Table 2). The pore size distribution estimated from the isotherms graphs 1501-1506 by using a non-local density functional theory (NLDFT) for M-VNU-93 materials was observed in around 24 Å, exhibiting a good agreement with the pore aperture metrics obtained from crystallographic data as shown in FIG. 3-FIG. 14 above. The pore volume estimated by using the BJH method increases from 0.23 to 0.39 $cm^3 g^{-1}$ with the trend Zn~Co<Mg<Ni~Fe<Cu. See Table 2.

TABLE 2

| Compound | BET ($m^2$ $g^{-1}$) | Langmuir ($m^2$ $g^{-1}$) | DFT PSD (Å) | Pore volume ($cm^3$ $g^{-1}$) | $CO_2$ uptake ($cm^3$ $g^{-1}$) | $Q_{st}$ (kJ $mol^{-1}$) |
|---|---|---|---|---|---|---|
| Mg-VNU-93 | 4052 | 4238 | 23 | 0.25 | 67.7 | 34.9 |
| Co-VNU-93 | 3246 | 3567 | 23 | 0.23 | 73.5 | 32.8 |
| Ni-VNU-93 | 3252 | 3473 | 23 | 0.33 | 70.6 | 35.7 |
| Zn-VNU-93 | 2729 | 3028 | 22 | 0.23 | 39.4 | 25.1 |
| Fe-VNU-93 | 3477 | 2424 | 22 | 0.33 | 42.4 | 17.7 |
| Cu-VNU-93 | 2125 | 1670 | 22 | 0.39 | 32.5 | 24.0 |

Referring next to FIG. 16-FIG. 21 which illustrate the $CO_2$ adsorption property of M-VNU-93 series at 273 K, 283 K, and 298 K respectively.

In FIG. 16-FIG. 21, the vertical axis represents the uptake or the amount of $CO_2$ adsorbed in a given pore unit volume ($cm^3/g$) and the horizontal axis represents the applied pressure in Torricelli (Torr.). At each specific temperature, an isotherm curve shows the relationship between $CO_2$ uptake and pressure.

Figure 16:
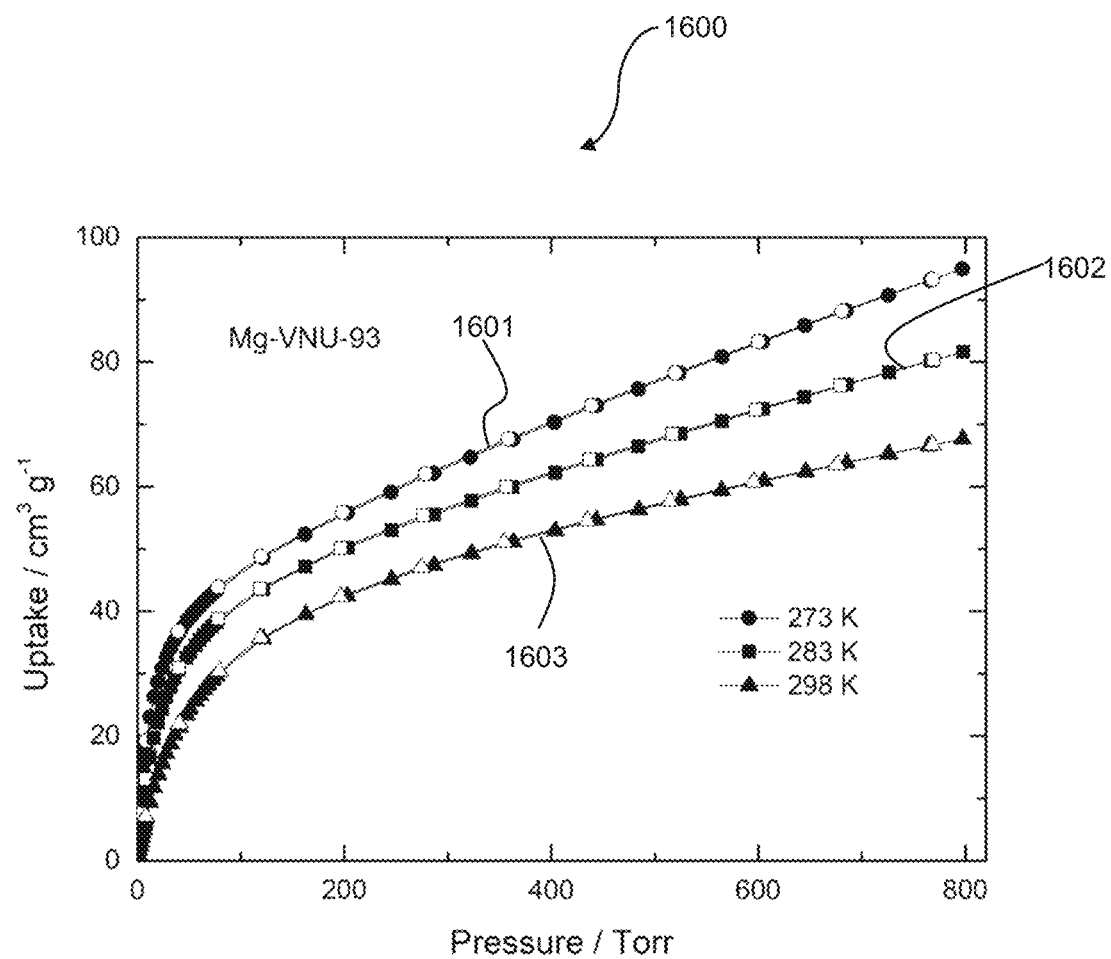
FIG. 16 are graphs of the $CO_2$ isotherms for Mg-VNU-93 at 273 K, 283 K, and 298 K in accordance with an aspect of the present invention.

Now referring to FIG. 16, a graph 1600 illustrates the $CO_2$ adsorption of for Mg-VNU-93 is shown. Graph 1600 which includes an isotherm curve 1601 at 273 K, an isotherm curve 1602 at 283 K, and an isotherm curve 1603 at 298 K. As seen from all three isotherm curves 1601, 1602, and 1603, they reveal the amount of $CO_2$ adsorption increased with the increasing pressure. That is, the higher the pressure the more $CO_2$ molecules can be adsorbed. On the other hand, the higher the temperature, the lower $CO_2$ molecules can be adsorbed due to the more kinetic energy that the $CO_2$ molecules receive from the increasing temperature. The isotherm curves 1601-1603 show that the adsorption and desorption curves of Mg-VNU-93 are reversible with the filled and blank dots on the same curve. The highest amount of $CO_2$ uptake is about 93 $cm^3/g$ at 800 Torr and the rapid increase in $CO_2$ uptake is between 0-50 Torr.

Figure 17:
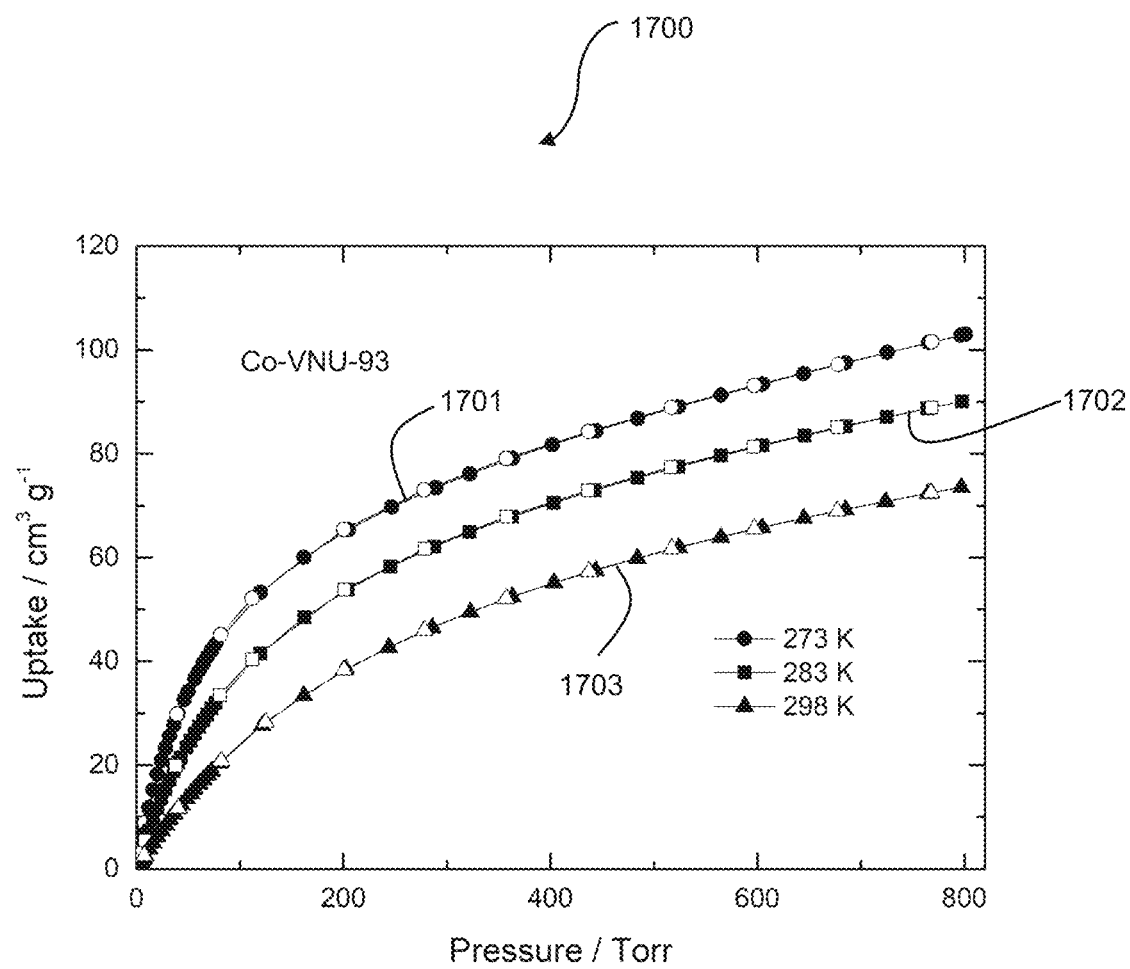
FIG. 17 are graphs of the $CO_2$ isotherms for Co-VNU-93 at 273 K, 283 K, and 298 K in accordance with an aspect of the present invention.

Now referring to FIG. 17, a graph 1700 illustrates the $CO_2$ adsorption of for Co-VNU-93 is shown. Graph 1700 which includes an isotherm curve 1701 at 273 K, an isotherm curve 1702 at 283 K, and an isotherm curve 1703 at 298 K. As seen from all three isotherm curves 1701, 1702, and 1703, they reveal the amount of $CO_2$ adsorption increased with the increasing pressure. That is, the higher the pressure the more $CO_2$ molecules can be adsorbed. On the other hand, the higher the temperature, the lower $CO_2$ molecules can be adsorbed due to the more kinetic energy that the $CO_2$ molecules receive from the increasing temperature. The isotherm curves 1701-1703 show that the adsorption and desorption curves of Co-VNU-93 are reversible with the filled and blank dots on the same curve. The highest amount of $CO_2$ uptake is about 103 $cm^3/g$ at 800 Torr and the rapid increase in $CO_2$ uptake is between 0-50 Torr.

Figure 18:
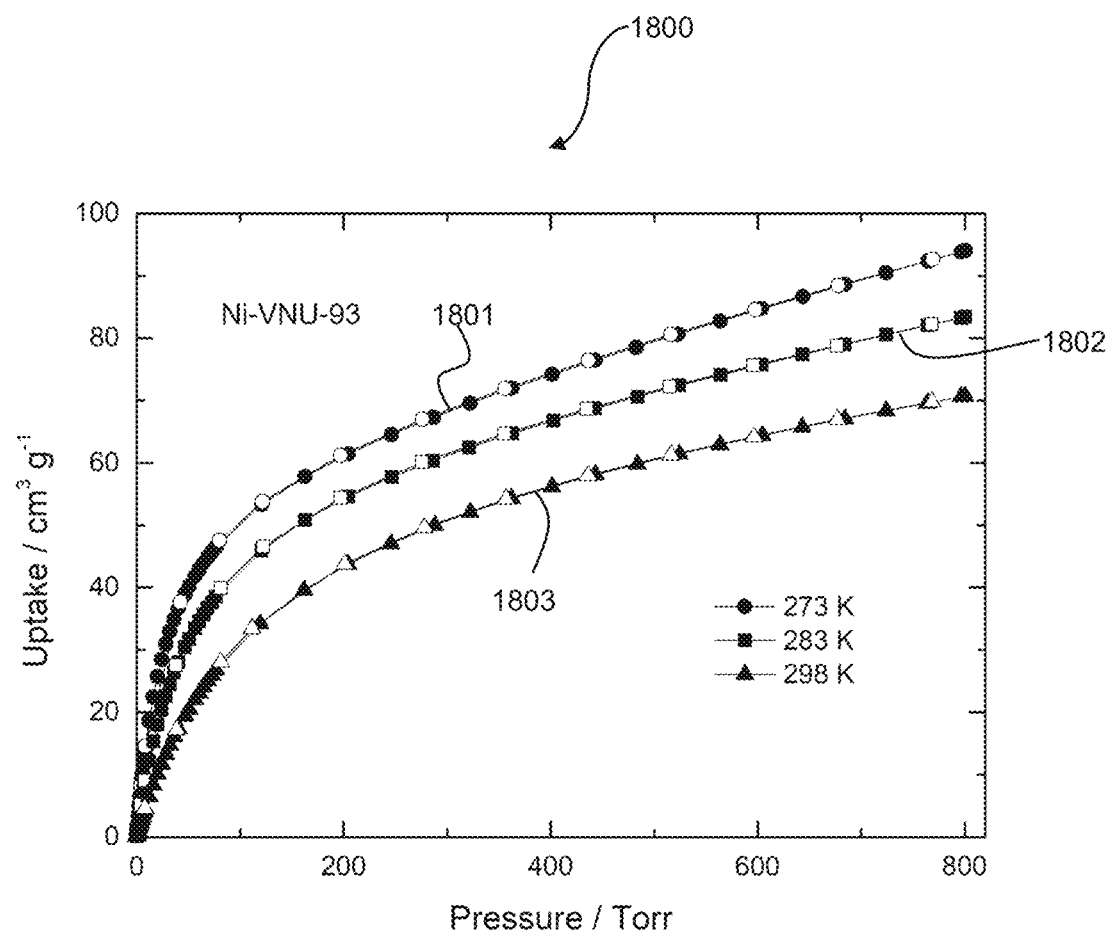
FIG. 18 are graphs of the $CO_2$ isotherms for Ni-VNU-93 at 273 K, 283 K, and 298 K in accordance with an aspect of the present invention.

Next referring to FIG. 18, a graph 1800 illustrates the $CO_2$ adsorption of for Ni-VNU-93 is shown. Graph 1800 which includes an isotherm curve 1801 at 273 K, an isotherm curve 1802 at 283 K, and an isotherm curve 1803 at 298 K. As seen from all three isotherm curves 1801, 1802, and 1803, they reveal that the amount of $CO_2$ adsorption increased with the increasing pressure. That is, the higher the pressure the more $CO_2$ molecules can be adsorbed. On the other hand, the higher the temperature, the lower $CO_2$ molecules can be adsorbed due to the more kinetic energy that the $CO_2$ molecules receive from the increasing temperature. The isotherm curves 1801-1803 show that the adsorption and desorption capacities of Ni-VNU-93 are the same—the filled and blank dots on the same curve. The highest amount of $CO_2$ uptake is about 93 $cm^3/g$ at 800 Torr and the rapid increase in $CO_2$ uptake is between 0-100 Torr.

Figure 19:
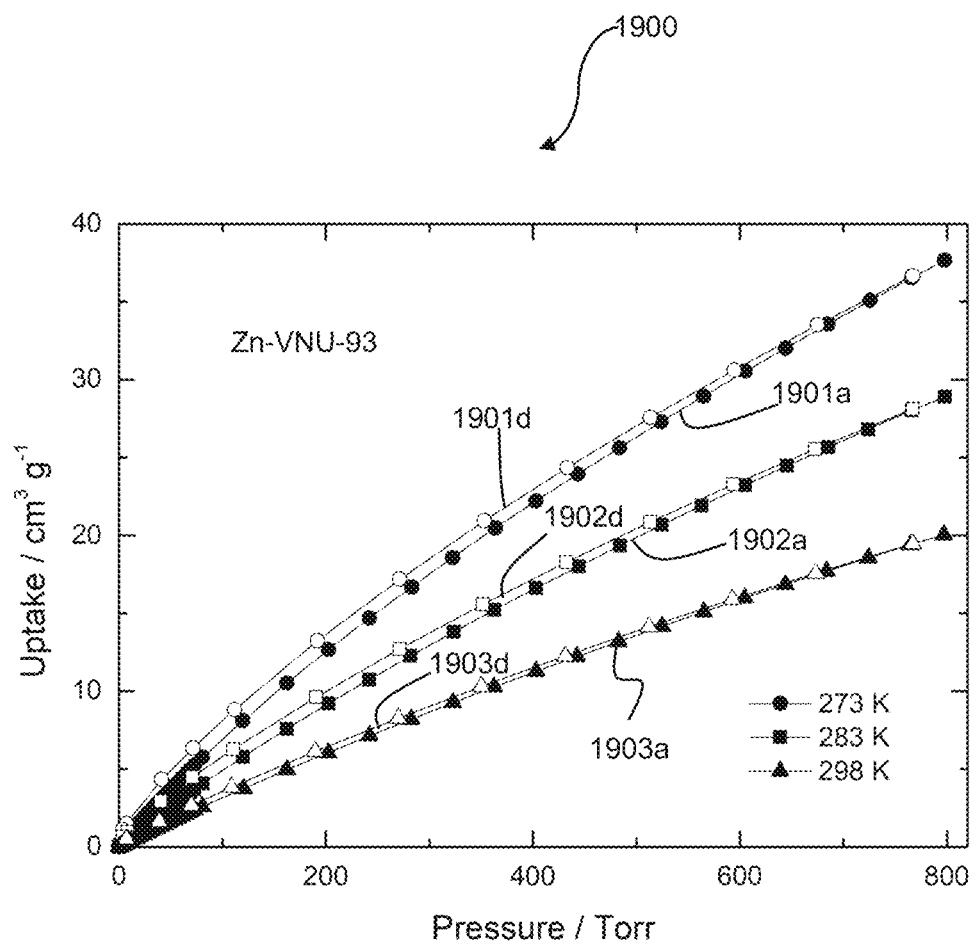
FIG. 19 are graphs of the $CO_2$ isotherms for Zn-VNU-93 at 273 K, 283 K, and 298 K in accordance with an aspect of the present invention.

Next referring to FIG. 19, a graph 1900 illustrates the $CO_2$ adsorption of for Zn-VNU-93 is shown. Graph 1900 which includes an isotherm adsorption curve 1901a and an isotherm desorption curve 1901d at 273 K, an isotherm adsorption curve 1902a and an isotherm desorption curve 1902d at 283 K, and an isotherm adsorption curve 1903a with an isotherm desorption curve 1903d at 298 K. As seen from all three isotherm curves 1901, 1902, and 1903, they reveal that the amount of $CO_2$ adsorption increased with the increasing pressure. That is, the higher the pressure the more $CO_2$ molecules can be adsorbed. On the other hand, the higher the temperature, the lower $CO_2$ molecules can be adsorbed due to the more kinetic energy that the $CO_2$ molecules receive from the increasing temperature. Isotherm curve 1901a at 273 K shows that the highest amount of $CO_2$ uptake is about 38 $cm^3/g$ at 800 Torr. All three isotherm curves 1901a-1903a show that the $CO_2$ adsorption of Zn-VNU-93 is linearly increasing with pressure.

Figure 20:
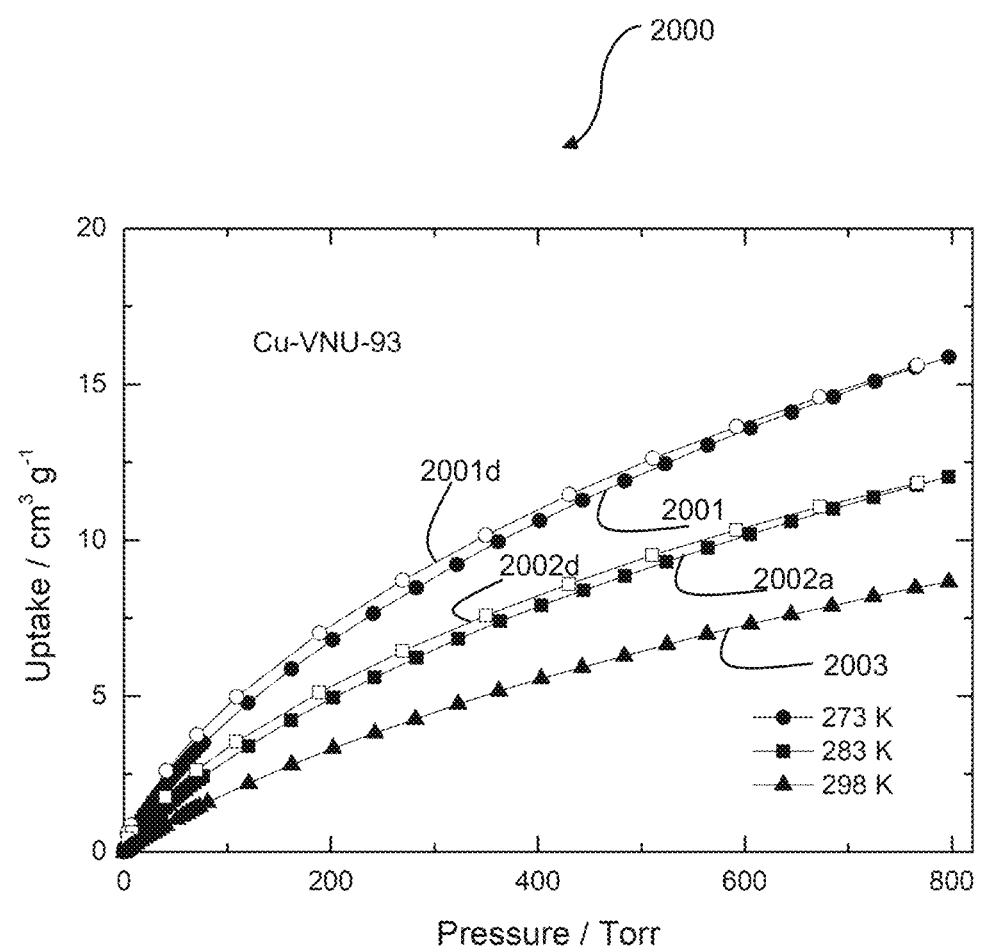
FIG. 20 are graphs of the $CO_2$ isotherms for Cu-VNU-93 at 273 K, 283 K, and 298 K in accordance with an aspect of the present invention.

Next referring to FIG. 20, a graph 2000 illustrates the $CO_2$ adsorption of for Cu-VNU-93 is shown. Graph 2000 which includes an isotherm adsorption curve 2001a and an isotherm desorption curve 2001d at 273 K, an isotherm adsorption curve 2002a and an isotherm desorption curve 2002 d at 283 K, and an isotherm adsorption curve 2003 at 298 K. As seen from all three isotherm curves 2001a, 2002 a, and 2003a, they reveal that the amount of $CO_2$ adsorption increased with the increasing pressure. That is, the higher the pressure the more $CO_2$ molecules can be adsorbed. On the other hand, the higher the temperature, the lower $CO_2$ molecules can be adsorbed due to the more kinetic energy that the $CO_2$ molecules receive from the increasing temperature. Isotherm curve 2001a at 273 K shows that the highest amount of $CO_2$ uptake is about 16 $cm^3/g$ at 800 Torr and the rapid increase in $CO_2$ uptake is between 0-100 Torr.

Figure 21:
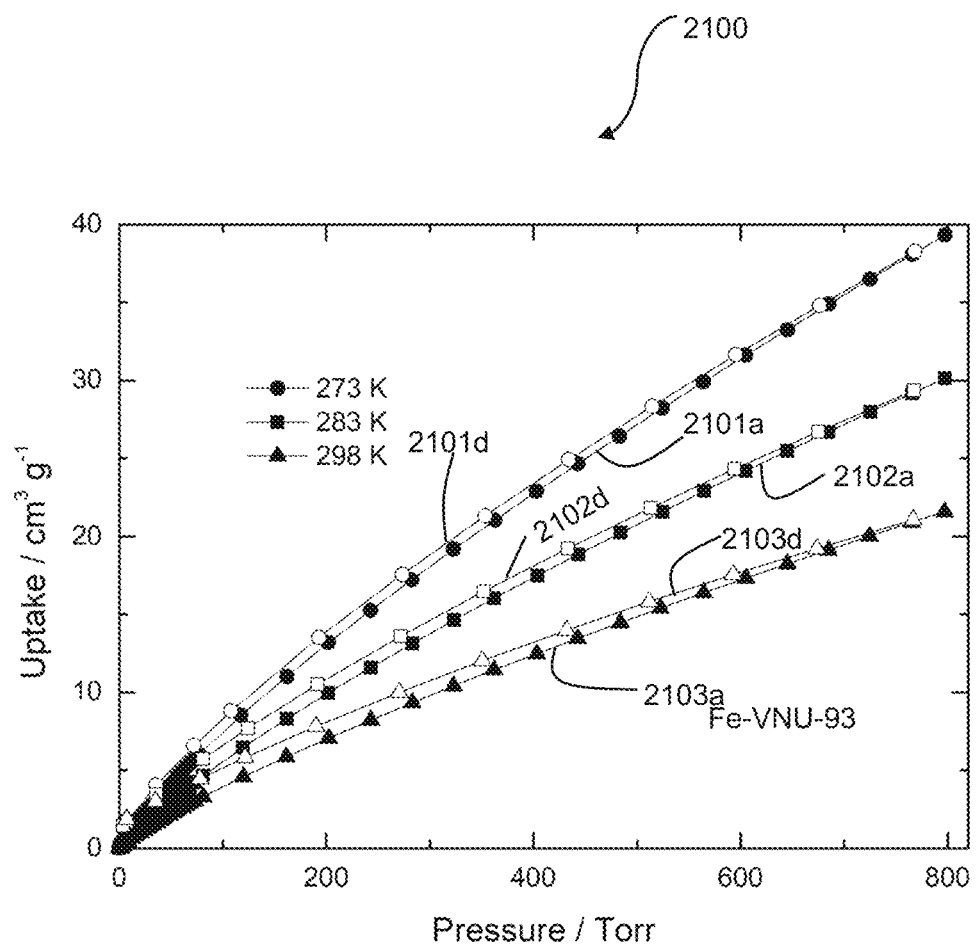
FIG. 21 are graphs of the $CO_2$ isotherms for Fe-VNU-93 at 273 K, 283 K, and 298 K in accordance with an aspect of the present invention.

Next referring to FIG. 21, a graph 2100 illustrates the $CO_2$ adsorption of for Fe-VNU-93 is shown. Graph 2100 includes an isotherm adsorption curve 2101a and an isotherm desorption curve 2101d at 273 K, an isotherm adsorption curve 2102a and an isotherm desorption curve 2102d at 283 K, and an isotherm adsorption curve 2103a with an isotherm desorption curve 2103d at 298 K. As seen from all three isotherm curves 2101a, 2102a, and 2103a, they reveal that the amount of $CO_2$ adsorption increased with the increasing pressure. That is, the higher the pressure the more $CO_2$ molecules can be adsorbed. On the other hand, the higher the temperature, the lower $CO_2$ molecules can be adsorbed due to the more kinetic energy that the $CO_2$ molecules receive from the increasing temperature. Isotherm curve 2101a at 273 K shows that the highest amount of $CO_2$ uptake is about 40 $cm^3/g$ at 800 Torr and the rapid increase in $CO_2$ uptake is between 0-100 Torr.

Summarizing FIG. 16-FIG. 21, Co-VNU-93 and Ni-VNU-93 reveal the highest $CO_2$ adsorption capacities of 73.5 and 70.6 $cm^3$ $g^{-1}$, respectively at 800 Torr and 298° K. The other members showed moderate $CO_2$ uptake and Zn-VNU-93 displayed the lowest $CO_2$ uptake (39.4 $cm^3$ $g^{-1}$) in the series. Furthermore, for Mg-VNU-93, Co-VNU-93, and Ni-VNU-93, the initial uptake in the low-pressure region of the $CO_2$ isotherms at 298 K is much steeper than those observed for Zn-VNU-93, Cu-VNU-93, and Fe-VNU-93. This is indicative of M-VNU-93 framework consisting $Mg^{2+}$, $Co^{2+}$, $Ni^{2+}$ ions expressing higher affinity to $CO_2$.

Figure 22:
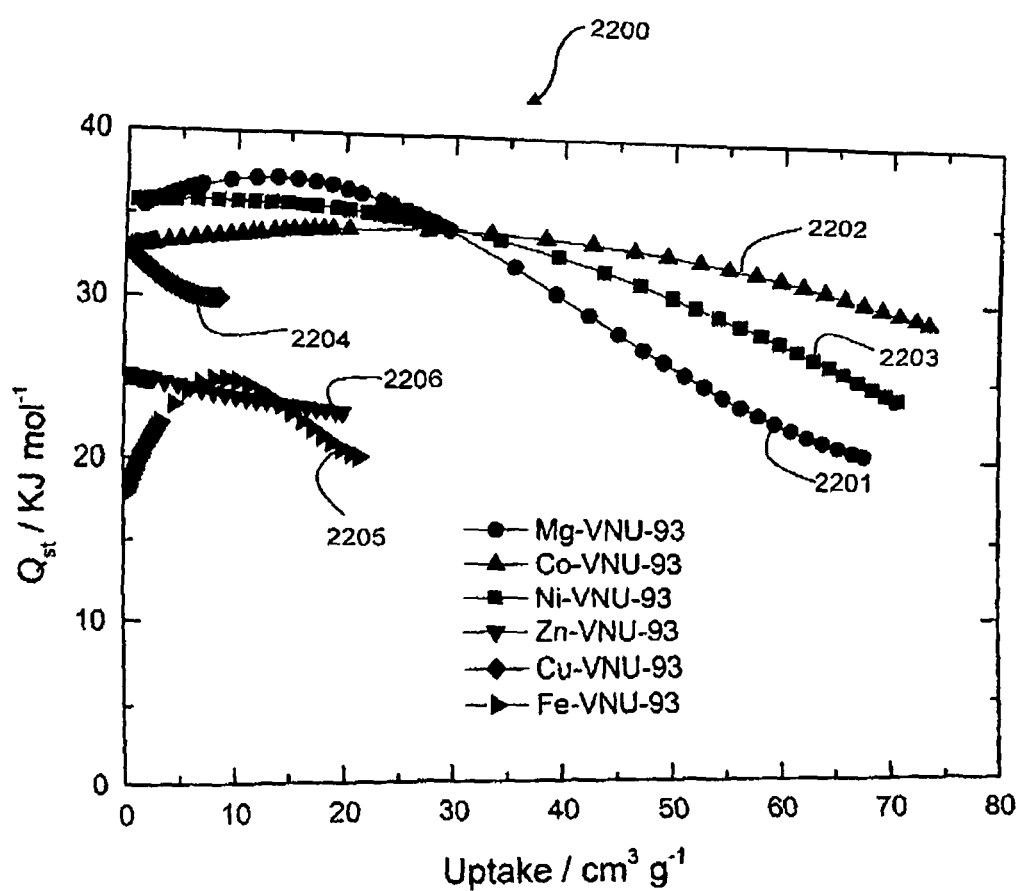
FIG. 22 are graphs illustrating the comparison of isosteric heat of adsorption $Q_{st}$ of $CO_2$ adsorption for M-VNU-93 series in accordance with an aspect of the present invention.

Motivated by the observation of FIG. 16-FIG. 21, the coverage-dependent isosteric heat of $CO_2$ adsorption ($Q_{st}$) by fitting the respective isotherms at 273, 283, and 298 K using a virial-type expansion equation is shown in FIG. 22. As expected, Ni-VNU-93, Mg-VNU-93, and Co-VNU-93 exhibited relatively higher $CO_2$ adsorption enthalpies at zero coverage (35.7, 34.9, and 32.8 kJ $mol^{-1}$, respectively) than the others.

Now referring to FIG. 22, a graph 2200 for the comparison of isosteric heat of adsorption ($Q_{st}$) of $CO_2$ adsorption for M-VNU-93 series in accordance with an aspect of the present invention is illustrated. Graph 2200 includes a $Q_{st}$ graph 2201 for Mg-VNU-93, a $Q_{st}$ graph 2202 for Co-VNU-93, a $Q_{st}$ graph 2203 for Ni-VNU-93, a $Q_{st}$ graph 2204 for Zn-VNU-93, a $Q_{st}$ graph 2205 for Fe-VNU-93, and a $Q_{st}$ graph 2206 for Cu-VNU-93. In the present invention, the coverage-dependent isosteric heat of $CO_2$ adsorption ($Q_{st}$) in graph 2200 is calculated by fitting the respective isotherms from FIG. 16-FIG. 21 at 273 K, 283 K, and 298 K using a virial-type expansion equation 2:

$$\ln P = \ln N + \frac{1}{T}\sum_{i=0}^{m} a_i N^i + \sum_{i=0}^{n} b_i N^i,$$

where P is pressure, N is the adsorbed amount, T is temperature, ai and bi are virial coefficient, and m and n are the number of virial coefficients required for adequate fitting of the isotherms. Accordingly, isosteric heat of adsorption ($Q_{st}$) at 298 K can be calculated by equation 3:

$$Q_{st} = -R\sum_{i=0}^{m} a_i N^i$$

Fitting parameters of the virial model are given in FIG. 22, the adsorption enthalpies ($Q_{st}$) expressed as a function of uptake is shown in graphs 2201-2206. As expected and shown in $Q_{st}$ graphs 2201-2206, Ni-VNU-93, Mg-VNU-93, and Co-VNU-93 exhibited relatively higher $CO_2$ adsorption enthalpies at zero coverage (35.7, 34.9, and 32.8 kJ mol$^{-1}$, respectively) than the other M-VNU-93 such as Zn-VNU-93, Fe-VNU-93, and Cu-VNU-93.

Figure 23:
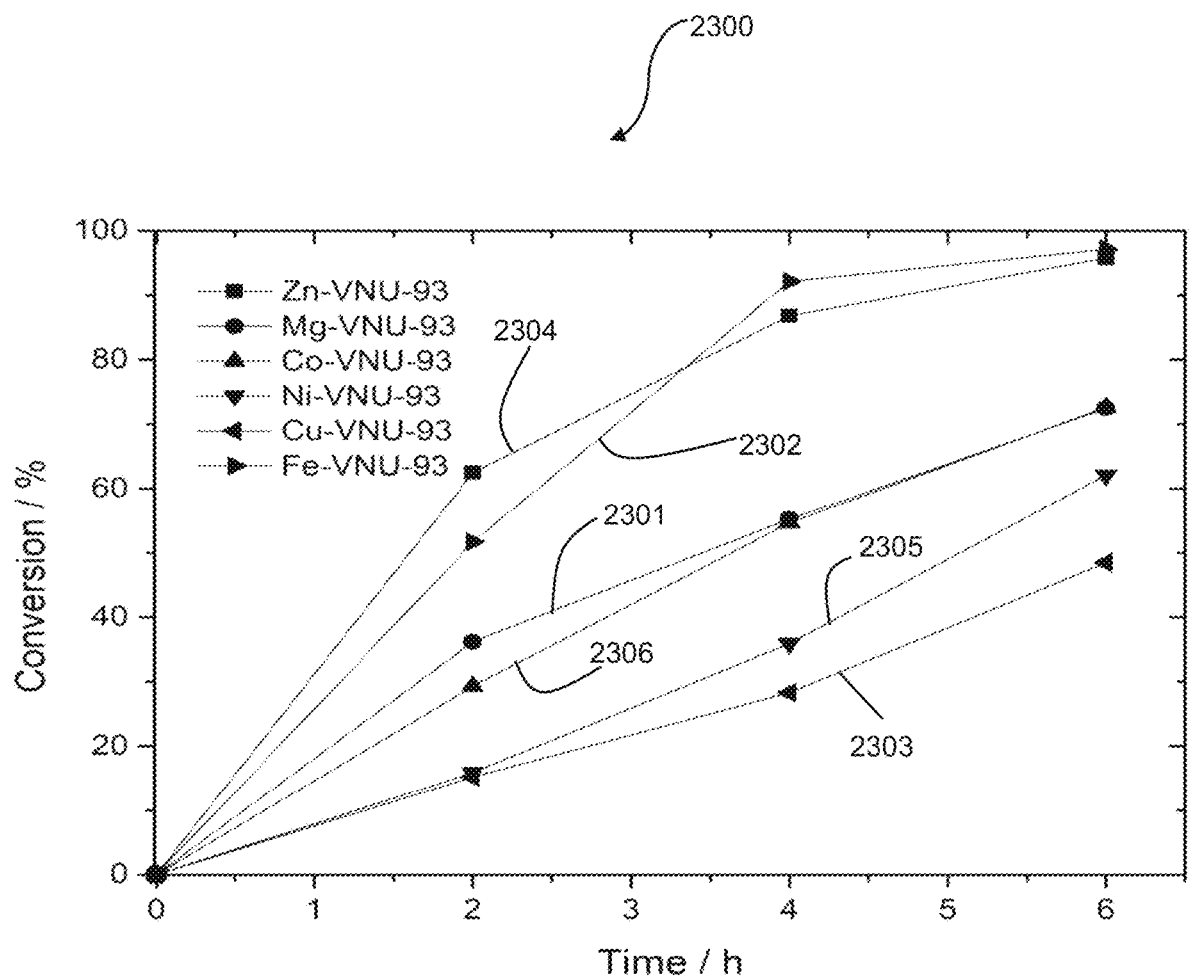
FIG. 23 are graphs illustrating the comparison of catalytic conversion of the styrene carbonate synthesis for M-VNU-93 series in accordance with an aspect of the present invention.

FIG. 23 is a graph 2300 illustrating the comparison of catalytic conversion of the styrene carbonate synthesis for M-VNU-93 series in accordance with an exemplary embodiment of the present invention. Graph 2300 includes a graph 2301 for Mg-VNU-93, a graph 2302 for Co-VNU-93, a graph 2303 for Ni-VNU-93, a graph 2304 for Zn-VNU-93, a graph 2305 for Fe-VNU-93, and a graph 2306 for Cu-VNU-93.

Figure 24:
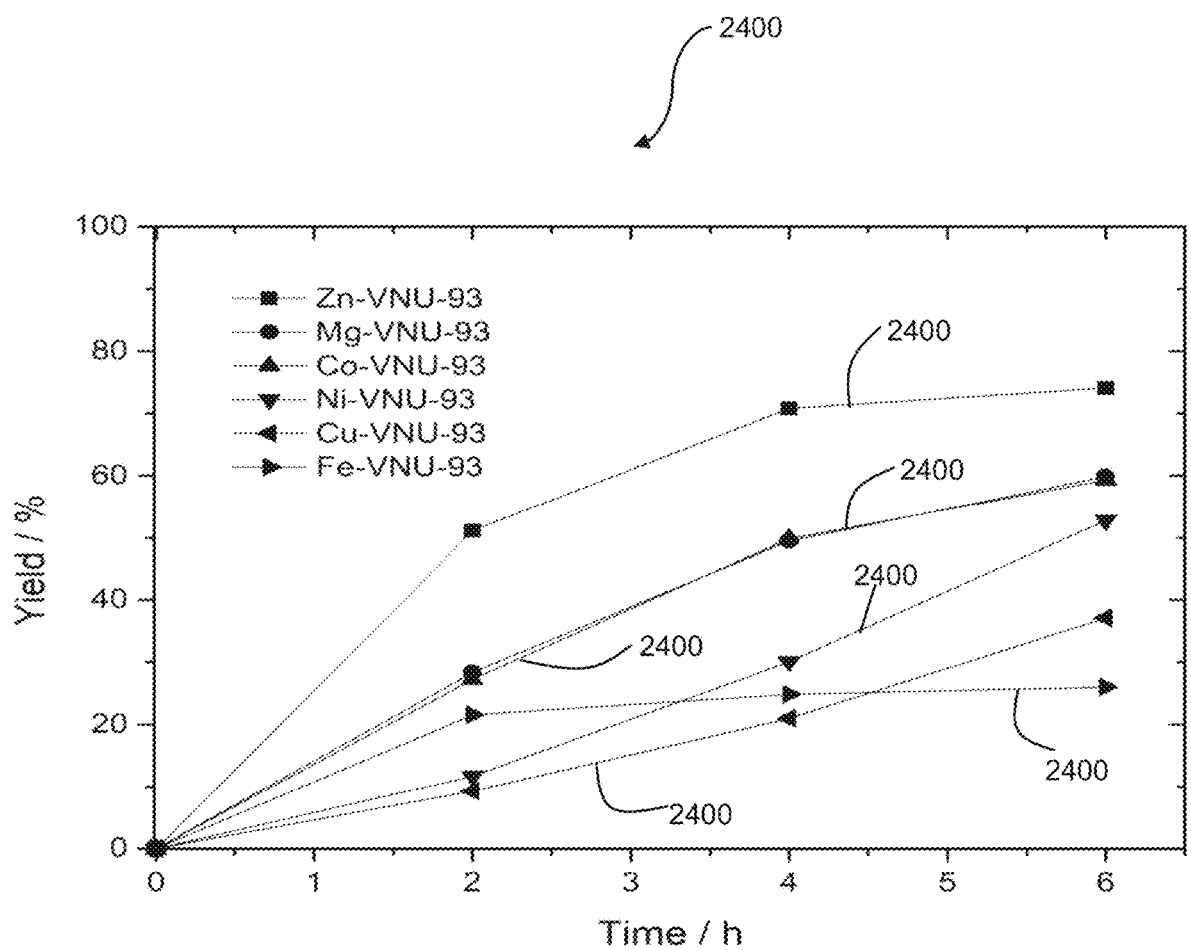
FIG. 24 are graphs illustrating the comparison of catalytic yield in the formation of styrene carbonate for M-VNU-93 series in accordance with an aspect of the present invention.

FIG. 24 is a graph 2400 illustrating the comparison of catalytic yield in the formation of styrene carbonate for M-VNU-93 series in accordance with an exemplary embodiment of the present invention. Graph 2400 includes a graph 2401 for Mg-VNU-93, a graph 2402 for Co-VNU-93, a graph 2403 for Ni-VNU-93, a graph 2404 for Zn-VNU-93, a graph 2405 for Fe-VNU-93, and a graph 2406 for Cu-VNU-93.

In principle, the open metal sites attributed from vary metal-oxo clusters $\{M_3[(-O)_3(-CO_2)_3]\}\infty$ (M=$Mg^{2+}$, $Zn^{2+}$, $Ni^{2+}$, $Co^{2+}$, $Fe^{2+}$, $Cu^{2+}$) constructing the M-VNU-93's framework serve as not only $CO_2$ binding sites but also different Lewis acid catalytic centers, could beneficial to $CO_2$ chemical fixation. The catalytic activity of M-VNU-93 toward the transformation of styrene oxide to styrene carbonate with $CO_2$ was investigated. Under the control experiment, Zn-VNU-93 demonstrated highly catalytic activity (conversion of 96%, a selectivity of 77%, and a yield of 74%) in forming styrene carbonate under a $CO_2$ pressure of 1 atm, after 6 hours at 80° C. (Table 1, FIGS. 23 & 24). Mg, Co-, Ni-VNU-93 exhibited high selectivity toward styrene carbonate (more than 82%), but they displayed lower conversions of styrene oxide (62-73%). Otherwise, Fe-VNU-93 showed the high catalytic conversion of styrene oxide (97%), but the yield of carbonate was found to be 26% and benzaldehyde was obtained as a main side-product of the oxidation process catalyzed by iron-based framework. In addition, Cu-VNU-93 was also found to be less active than other MOFs with a 38% yield of styrene carbonate after 6 hours. As depicted in Table 3, all M-VNU-93 have catalytic activity on the cycloaddition of $CO_2$ and styrene oxide which were significantly higher than that of MOF-free reaction.

TABLE 3

Synthesis of styrene carbonate from $CO_2$ and styrene using M-VNU-93[a]

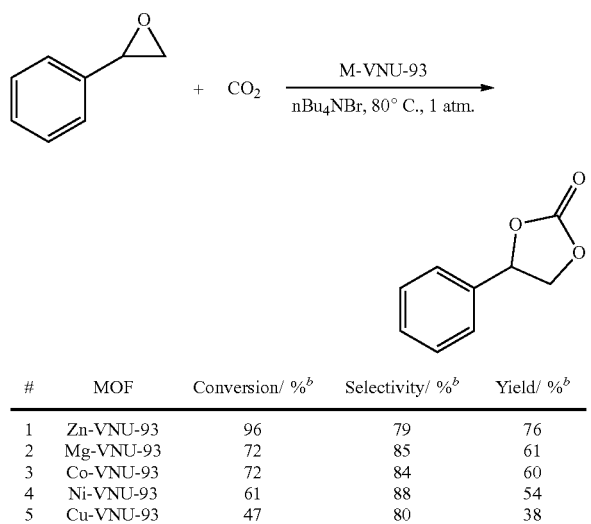

| # | MOF | Conversion/ %[b] | Selectivity/ %[b] | Yield/ %[b] |
|---|---|---|---|---|
| 1 | Zn-VNU-93 | 96 | 79 | 76 |
| 2 | Mg-VNU-93 | 72 | 85 | 61 |
| 3 | Co-VNU-93 | 72 | 84 | 60 |
| 4 | Ni-VNU-93 | 61 | 88 | 54 |
| 5 | Cu-VNU-93 | 47 | 80 | 38 |

TABLE 3-continued

| 6 | Fe-VNU-93 | 97 | 27 | 26 |
| 7 | None | 20 | 65 | 13 |

[a]Reaction conditions: styrene oxide (5 mmol), MOF catalyst (1.2 mol % based on metal active site), nBu$_4$NBr (1.5 mol %), 1 atm $CO_2$ (balloon pressure), 80° C., and 6 hours.
[b]The conversion, selectivity, and yield were determined by GC-FID analysis using biphenyl as the internal standard.

Figure 25:
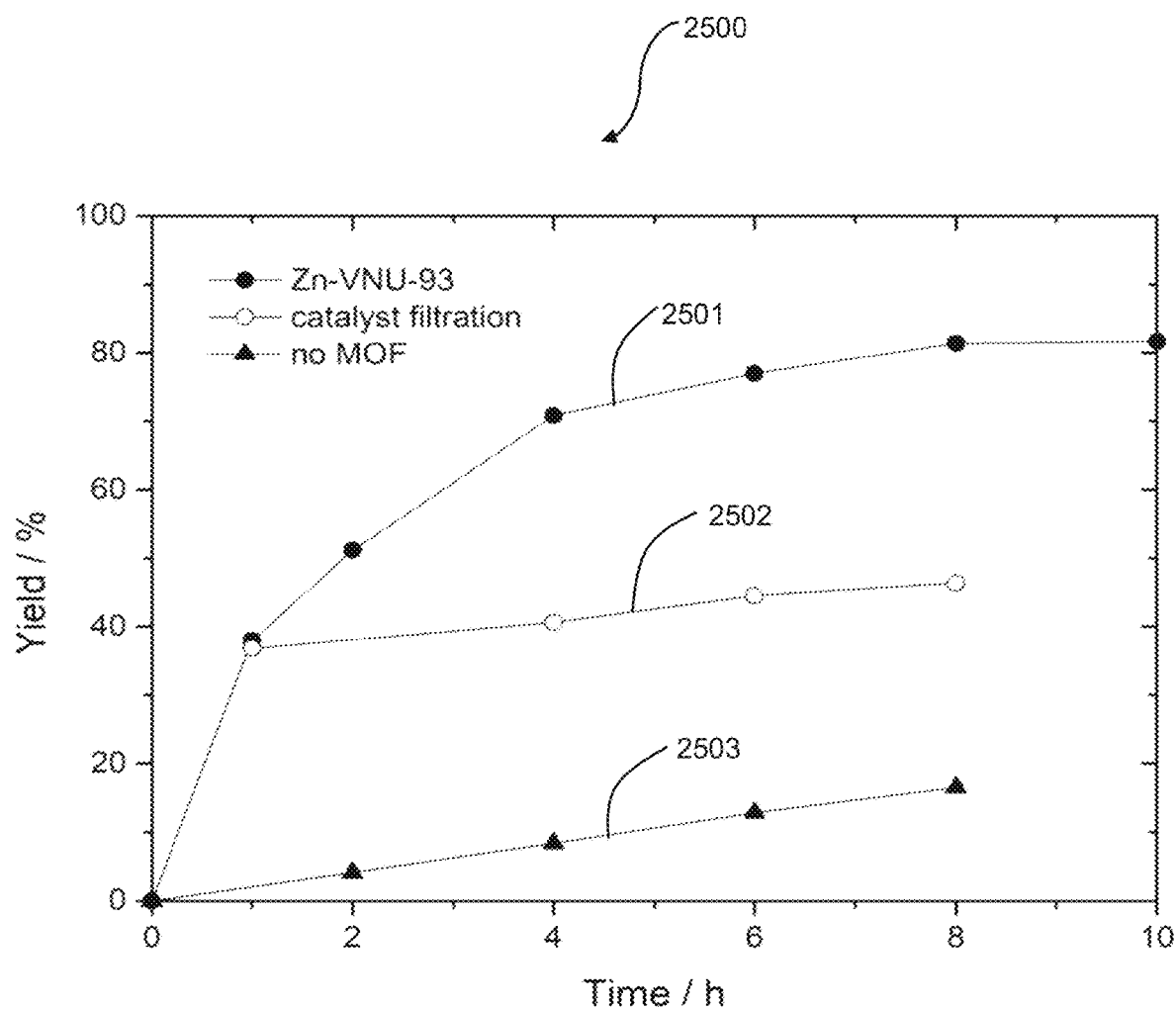
FIG. 25 are graphs illustrating the comparison of catalytic yield in the formation of styrene carbonate with the presence of Zn-VNU-93, after filtration of Zn-VNU-93 catalyst, and without MOF catalyst in accordance with an aspect of the present invention.

FIG. 25 is a graph 2500 illustrating the comparison of catalytic yield in the formation of styrene carbonate with the presence of Zn-VNU-93 in a graph 2501, after filtration of Zn-VNU-93 catalyst as shown in a graph 2502, and without MOF catalyst as in a graph 2503. The activity of the most efficient catalyst in the series, Zn-VNU-93, was then evaluated in more depth. As such, in the model reaction, upon elongating the reaction time to 8 hours, Zn-VNU-93 afforded the highest conversion of styrene oxide, selectivity and yield of styrene carbonate (96, 84, and 81%, respectively). A further increase the reaction time to 10 hours was found to be ineffective, resulting in the same catalytic performance to that of 8 hours (FIG. 25). To assess the heterogeneous nature of Zn-VNU-93, a leaching experiment was performed to prove that there is no significant catalytic activity promoted from $Zn^{2+}$ ions leaching from the Zn-VNU-93 structure. Accordingly, in an after the catalytic reactions were carried out for 1 hour, Zn-VNU-93 catalyst was removed by centrifugation, and the filtrated reaction was allowed to continue for 8 hours. As expected, there was no significant increase in the yield of styrene carbonate (46%) from the filtration reaction.

Zn-VNU-93 was also compared the catalytic activity with other homogeneous and heterogeneous catalysts, as well as other Lewis acidic-MOF materials under the same condition reaction for the conversion of styrene oxide to styrene carbonate (Table 4). Zn-VNU-93 again showed superior catalytic performance compared with the other catalysts. As such, the homogeneous metal salts, $Zn(NO_3)_2 \cdot 6H_2O$, $Zn(CH_3COO)_2 \cdot 2H_2O$, and heterogeneous materials, ZnO, Zn exhibited lower yields of 50, 32, 28, and 19%, respectively, than those of Zn-VNU-93. Other MOF catalysts containing Lewis acid sites including a benchmark series M-MOF-74 (M=Mg, Co, Zn) and Zn-based MOFs such as MOF-5, MOF-177, and ZIF-8 were performed under a model reaction. Accordingly, M-MOF-74 compounds promoted the outstanding selectivities in styrene carbonate synthesis (>80%), but relative low conversions of styrene oxide (27-30%), except Zn-MOF-74 (conversion of 88%). MOF-5 and Zn-MOF-74 promoted the reactions with moderate yields of 70%, while MOF-177, Co-MOF-74, Mg-MOF-74 and ZIF-8 catalyzed low yields of 42, 28, 24, and 24%, respectively. These results implies the catalysis outperformance of Zn-VNU-93 in the cycloaddition of $CO_2$ and styrene oxide.

TABLE 4

Comparison of Catalysts for Cycloaddition of Styrene Oxide and $CO_2$[a]

| Type | Catalyst | conversion.[c] /% | selectivity.[c] /% | yield.[c] /% |
|---|---|---|---|---|
| MOF | Zn-VNU-93 | 96 | 86 | 82 |
| | Mg-VNU-93 | 66 | 96 | 63 |
| | Co-VNU-93 | 67 | 99 | 66 |
| | Ni-VNU-93 | 59 | 100 | 59 |
| | Cu-VNU-93 | 47 | 80 | 38 |
| | Fe-VNU-93 | 97 | 27 | 26 |
| | Zn-MOF-74 | 88 | 80 | 70 |
| | Mg-MOF-74 | 27 | 91 | 24 |
| | Co-MOF-74 | 31 | 91 | 28 |

TABLE 4-continued

Comparison of Catalysts for Cycloaddition of Styrene Oxide and $CO_2$[a]

| Type | Catalyst | conversion.[c] /% | selectivity.[c] /% | yield.[c] /% |
|---|---|---|---|---|
|  | MOF-5 | 83 | 84 | 70 |
|  | MOF-177 | 56 | 75 | 42 |
|  | ZIF-8 | 28 | 86 | 24 |
| het. | Zn | 62 | 93 | 57 |
|  | ZnO | 60 | 91 | 55 |
| hom. | $Zn(NO_3)_2·6H_2O$ | 37 | 63 | 24 |
|  | $Zn(CH_3COO)_2·2H_2O$ | 46 | 71 | 32 |

[a]Reaction conditions: styrene oxide (5 mmol), MOF catalyst (1.2 mol % based on metal active site), nBu₄NBr (1.5 mol %), 1 atm $CO_2$ (balloon pressure), 80° C., and 6 hours.
[b]The conversion, selectivity, and yield were determined by GC-FID analysis using biphenyl as the internal standard.
het. = heterogeneous;
hom. = homogeneous.

Figure 26:
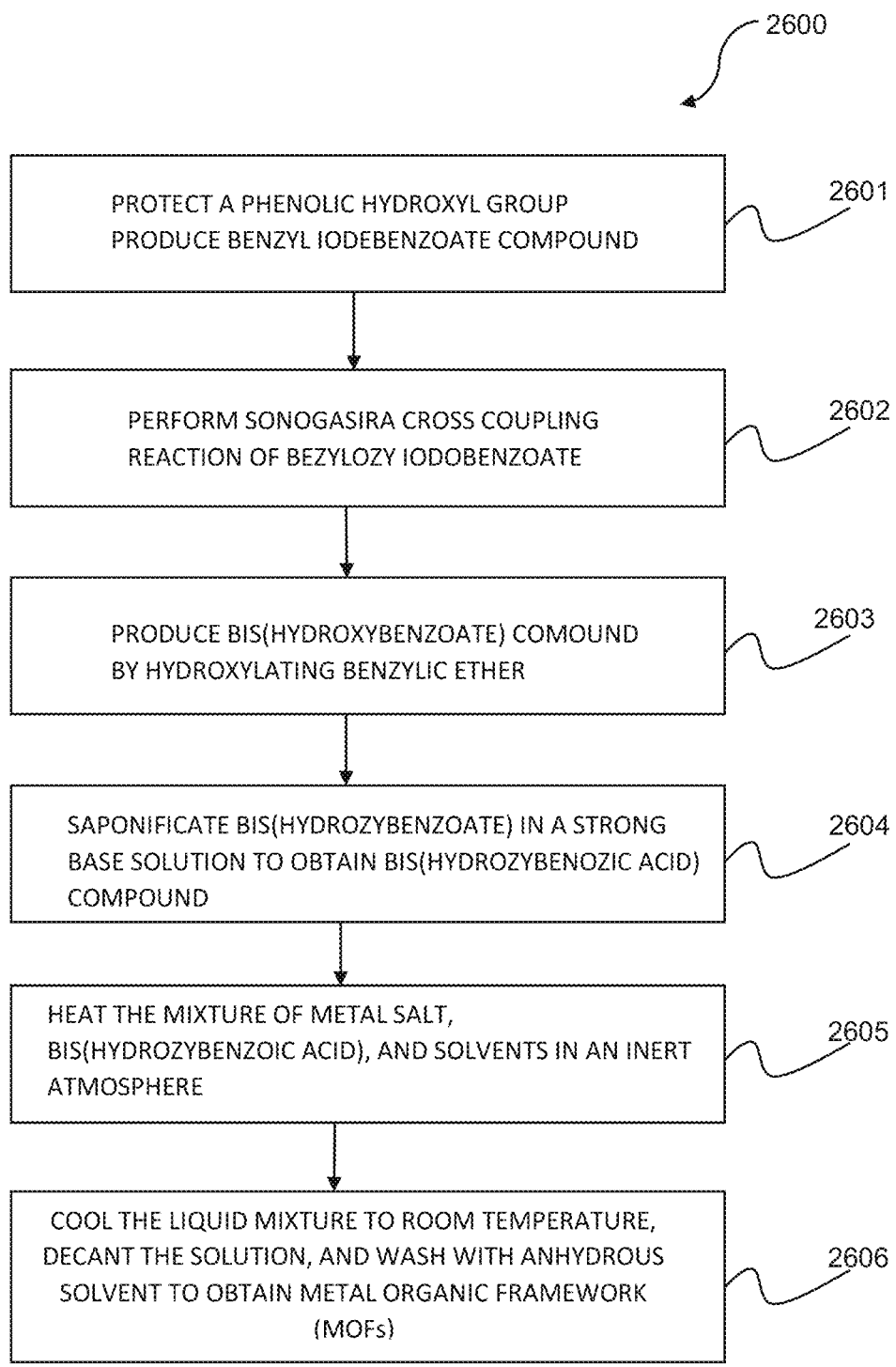
FIG. 26 is a flow chart of a process for synthesizing the M-VNU-93 series in accordance with an exemplary embodiment of the present invention.

Referring to FIG. 26, a process 2600 for synthesizing the Metal-Organic Framework (MOF) termed as M-VNU-93 is illustrated. In various embodiments of the present invention, multi-step chemical reaction 2600 includes a protection step 2601 for protecting a hydroxyl group (—OH) in an alcohol compound, a cross-coupling step 2602 of the resulting compound obtained in step 2601, a cleavage step 2603 of the compound obtained in step 2602, a bis(hydroxybenzoate) compound is produced using hydroxylating benzylic ether in a step 2604, bis(hydroxybenzoate) is saponificated in a strong base to obtain bis(hydroxybenzoic acid) compound at a step 2604, then at a step 2605 bis(hydroxybenzoic acid is mixed with metal salt and heated in an inert atmosphere, finally at a step 2606 M-VNU-93 is obtained by cooling, decanting, and washing the liquid mixture with anhydrous solvent at room temperature.

More particularly, in protection step 2601, a hydroxyl group (—OH) is protected by a protection reaction between a protection group and a functional group. In an exemplary implementation of protection step 2601, the phenolic hydroxyl alcohol is protected or masked using a benzylic ether (OBn) protection group by performing the reaction of methyl hydroxy iodobenzoate and benzyl bromide (BnBr) to produce benzyloxy iodobenzoate compound. Benzyl bromide (BnBr) and potassium carbonate ($K_2CO_3$) are used as reagents and acetonitrile (MeCN) is used as a solvent in temperature around 80° C. for 24 hours. Benzyl ether group (OBn) is attached to hydroxyl (OH) to form benzyloxy iodobenzoate that is stable to subsequent reaction steps 2602-2604.

Next in cross-coupling step 2602, cross-coupling reaction is performed with the aid of metal catalysts to form a carbon-carbon bond between the compounds obtained in the protection step 2601 above. In various implements of cross-coupling step 2602, the Sonagashira cross-coupling is performed on the benzyloxy iodobenzoate obtained in step 2601 with the aid of transition metal such as palladium (Pd) as catalyst and copper (Cu) as cocatalyst. Step 2602 involves a palladium cycle and a copper cycle in which the final product is ethyne bis(benzyloxy benzoate).

In cleavage or hydroxylation step 2603, hydroxylating of benzylic ether (OBn) in bis(benzyloxybenzoate) compound is performed. In other words, hydroxylation step 2603 introduces the hydroxyl (—OH) group into the bis(benzyloxybenzoate) to obtain bis(hydroxybenzoate). The oxygen-carbon bond of benzylic ether (OBn) is replaced by a oxygen-hydrogen bond of the hydroxyl (—OH) in the bis(benzyloxybenzoate) compound in a dicloromethane ($CH_2Cl_2$) solvent using an organosilicon reagent such as trimethylsilyl iodine (TMSI).

In step 2604, bis(hydroxybenzoate) is saponificated in a strong base solution to obtain bis(hydroxybenozic acid). In various aspects of the present invention, NaOH is used as the strong base and is added in a solution of the bis(hydroxybenzoate) compound in tetrahydrofuran/methanol (THF/MeOH) solution. The reaction mixture is stirred at 60° C. for 24 hours. Then, the mixture is acidified with hydrochloride acid (HCl) (1 mole) to obtain EDHB linker or ligand.

In steps 2605 and 2606, M-VNU-93 Metal-Organic Framework (MOF) is formed by allowing metal salt and EDHB linker contacting with a mixture solvent of N, N'-dimethylformamide (DMF) and methanol, or ethanol, or water. The medium was capped in an 8 mL vial and heated at elevated temperature. At the completion of step 2606, the mother solution is decanted and the MOF (M-VNU-93) is washed with DMF to remove any residues including unreacted linker and metal salts which are then soaked in a volatile solvent including anhydrous methanol. The decantation of methanol is followed and the MOF solid is evacuated under vacuum at ambient temperature for 24 hours, followed by heating at 100° C. for an additional 24 hours.

EXAMPLES

1. General Procedures, Instruments, and Materials

All reagents and solvents were commercially purchased and used without further purification unless otherwise specified. $^1H$ NMR and $^{13}C$ NMR were recorded on a Bruker Advance 11-500 MHz NMR spectrometer using tetramethylsilane as an internal standard. Chemical shifts were quoted in parts per million (ppm) and coupling constants, J, were reported in Hertz (Hz). Powder X-ray diffraction (PXRD) data were collected using a Bruker D8 Advance employing Ni-filtered Cu Kα (λ=1.54178 Å).

Field-emission Scanning Electron Microscope (FE-SEM) was performed on M-VNU-93 samples dispersed onto a sticky carbon surface attached to a flat aluminium sample holder. FE-SEM images were taken on an ultralow voltage Hitachi's S-4800 FE-SEM operating at an accelerating voltage of 1 kV. A Micromeritics 3Flex surface analyzer was used to measure gas adsorption-desorption isotherms. A liquid-$N_2$ bath was used for measurements at 77 K, and a water circulator was used for measurements at 273 K, 283 K, and 298 K. For all sorption measurements, Helium (He) was used to estimate the dead space. An Agilent gas chromatography (GC) System 19091s-433 equipped with a mass selective detector Agilent 5973N instrument (GC-MS) was used to confirm the products using a capillary HP-5MS 5% phenyl methyl siloxane column (30 m×250 μm×0.25 μm). The conversion, selectivity, and yield of catalytic reactions were determined by the Agilent GC system 123-0132 equipped with a flame ionization detector (FID) and a capillary DB-1 ms column (30 m×320 μm×0.25 μm). Biphenyl was used as an internal standard for the catalytic studies.

2. Synthesis of Organic Linker

Synthesis of Methyl 2-(benzyloxy)-4-iodobenzoate ("Compound 2")

Compound 2 was prepared by following procedure: [5] (See *Science*, 2012, vol. 336, pp. 1018). H-NMR (500 MHz, DMSO-$d_6$): $δ_H$=7.61 (d, J=1.0 Hz, 1H), 7.47 (t, J=7.7 Hz, 2H, H-1, H-2), 7.43 (m, 2H), 7.39 (m, 2H), 7.32 (t, J=7.4 Hz, 1H). $^{13}C$ NMR (125 MHz, DMSO-$d_6$): $δ_C$=165.5, 157.5, 136.5, 132.2, 129.5, 128.3, 127.7, 126.9, 122.9, 119.9, 100.6, 69.9, 51.9 ppm. Please refer again to FIG. 1 and FIG. 26.

Synthesis of Dimethyl 4,4'-(ethyne-1,2-diyl)bis(2-(benzyloxy)benzoate) (Product 3)

In a $N_2$ atmosphere, a 250 mL Schlenk flask was charged with $Pd(PPh_3)_2Cl_2$ (0.23 g, 0.12 mmol), CuI (0.124 g, 0.24 mmol), and methyl 2-(benzyloxy)-4-iodobenzoate 2 (6 g, 6 mmol). Triethylamine (TEA) (80 mL, 0.21 mmol) and DBU (16 mL, 39.6 mmol) were then added and stirred rapidly before trimethylsilylacetylene (1.15 mL, 3.0 mmol) was added via a gas-tight syringe to initiate the reaction. Degassed and deionized water (0.1 mL, 2.4 mmol) was then introduced to the reaction flask, and then the reaction was covered with aluminium foil and allowed to stir under $N_2$ at ambient temperature overnight. DCM (250 mL) was added to the resulting mixture which was further extracted with a saturated $NH_4Cl$ solution (3×150 mL). The organic layer was dried over anhydrous $Na_2SO_4$ and concentrated under reduced pressure to obtain the crude brown-orange solid. The crude solid was absorbed on silica-gel and subjected to column chromatography (hexane:$CH_2Cl_2$=1:1) to obtain a dark brown solid. This solid was further recrystallized from ($Et_2O$:$CH_2Cl_2$=9:1), filtered, and dried in air to afford the white product 3 (75% yield, 4.5 g). $^1$H-NMR (500 MHz, DMSO-$d_6$): $\delta_H$=7.76 (d, J=7.9 Hz, 2H), 7.51 (d, J=7.4 Hz, 4H), 7.45 (d, J=1.1 Hz, 2H), 7.42 (t, J=7.6 Hz, 4H), 7.34 (t, J=7.3 Hz, 2H), 7.26 (dd, J=7.9 Hz, 1.3 Hz, 2H), 5.28 (s, 4H), 3.83 (s, 6H).). $^{13}$C NMR (125 MHz, DMSO-$d_6$): $\delta_C$=165.4, 157.1, 136.6, 131.2, 128.4, 127.7, 126.9, 126.5, 123.7, 121.0, 116.6, 90.5, 69.8, 52.0 ppm.

Synthesis of Dimethyl 4,4'-(ethyne-1,2-diyl)bis(2-hydroxybenzoate) (Product 4)

In a $N_2$ atmosphere, a dry Schlenk flask was charged with dimethyl 4,4'-(ethyne-1,2-diyl)bis(2(benzyloxy)benzoate) 3 (2 g, 3.95 mmol) and DCM (20 mL) to give a clear solution. The reaction was covered with aluminium foil. Trimethylsilyl iodide (TMSI, 5 mL, 6.5 mmol) was inserted in the reaction via a dry syringe. The reaction was stirred at room temperature for 4 hours and monitored by TLC analysis for the given period of time. At the completion of the reaction, the excess trimethylsilyl iodide was decomposed by pouring into the reaction a 20 mL of methanol. Subsequently, the mixture was continued to stir at room temperature for 16 hours to afford an insoluble solid which was further filtered and washed with MeOH yielding the white product 4. The filtrated brown solution was further evaporated under reduced pressure to obtain the dark yellow product which was further recrystallized from (EtOH:$CH_2Cl_2$=9:1), filtered and dried in air to afford the white product 4 (50% yield, g). $^1$H-NMR (500 MHz, DMSO-$d_6$): $\delta_H$=10.58 (s, 2H), 7.81 (d, J=8.1 Hz, 2H), 7.18 (d, J=1.3 Hz, 2H), 7.13 (dd, J=8.1 Hz, 1.5 Hz, 2H), 3.90 (s, 6H). $^{13}$C NMR (125 MHz, DMSO-$d_6$): $\downarrow_C$=168.2, 159.3, 130.6, 128.0, 122.4, 120.0, 114.3, 90.6, 52.5 ppm.

Synthesis of 4,4'-(ethyne-1,2-diyl)bis(2-hydroxybenzoic Acid) (Product 5)

A 100 mL round bottom flask was charged with dimethyl 4,4'-(ethyne-1,2-diyl)bis(2hydroxybenzoate) 4 (1.1 g, 3.37 mmol), NaOH (4.05 g, 101.2 mmol) and a MeOH/THF (30 mL:30 mL) mixture, which was then stirred and refluxed at 80° C. for 1 day. The reaction mixture was subsequently cooled to room temperature and a distilled water (50 mL) was added until the entire mixture became a clear homogeneous solution. This solution was filtered to remove any residues remaining. The filtrate aqueous solution was acidified with concentrated aqueous HCl (1 M) to precipitate the solid until the pH ~1. The solid was filtered over a Buchner funnel and washed thoroughly with distilled water until the filtrate was no longer acidic. The wet solid was then dried in air at 85° C. overnight to afford the white product 5 (EDHB linker) (50% yield, g). $^1$H-NMR (500 MHz, DMSO-$d_6$): $\delta_H$=7.82 (d, J=8.1 Hz, 2H), 7.15 (d, J=1.4 Hz, 2H), 7.11 (dd, J=8.1 Hz, 1.5 Hz, 2H). $^{13}$C NMR (125 MHz, DMSO-$d_6$): $\delta_C$=171.2, 160.7, 130.7, 128.3, 122.3, 119.7, 113.8, 90.7 ppm.

3. Synthesis of M-VNU-93 Series

Synthesis of Mg-VNU-93

Step 2605 and step 2606 are implemented by the following procedure. A 0.1 M stock solution of magnesium nitrate hexahydrate ($Mg(NO_3)_2 \cdot 6H_2O$) in DMF was added to an 8 mL vial, which was preloaded with EDHB linker (0.057 mmol). This was followed by the addition of a mixture of DMF:EtOH:$H_2O$ (v:v:v=8:1:1) to the vial. The vial was capped tightly, quickly sonicated and heated at 120° C. for 24 hours, yielding a beige solid. The mother solution was decanted and the powder was then washed thoroughly with DMF (3×5 mL) per day for 3 days, then soaked in anhydrous MeOH (3×5 mL) per day for 3 days total. The solvent-exchanged sample was desolvated under vacuum at ambient temperature for 24 hours, followed by heating at 100° C. under vacuum for an additional 24 hours. Please refer back to step 2605 and step 2606 in FIG. 26.

Synthesis of Ni-VNU-93

Step 2605 and step 2606 are implemented by the following procedure. A 0.1 M stock solution of nickel nitrate hexahydrate ($Ni(NO_3)_2 \cdot 6H_2O$) in DMF was added to an 8 mL vial, which was preloaded with EDHB linker (0.054 mmol). This was followed by the addition of a mixture of DMF:EtOH:$H_2O$ (v:v:v=8:1:1) to the vial. The vial was capped tightly, quickly sonicated and heated at 120° C. for 24 hours, yielding a green solid. The mother solution was decanted and the powder was then washed thoroughly with DMF (3×5 mL) per day for 3 days, then soaked in anhydrous MeOH (3×5 mL) per day for 3 days total. The solvent-exchanged sample was desolvated under vacuum at ambient temperature for 24 hours, followed by heating at 100° C. under vacuum for an additional 24 hours. Please refer back to step 2605 and step 2606 in FIG. 26.

Synthesis of Co-VNU-93

Step 2605 and step 2606 are implemented by the following procedure. A 0.1 M stock solution of cobalt nitrate hexahydrate ($Co(NO_3)_2 \cdot 6H_2O$) in DMF was added to an 8 mL vial, which was preloaded with EDHB linker (0.057 mmol). This was followed by the addition of a mixture of DMF:EtOH:$H_2O$ (v:v:v=0.5:1:1) to the vial. The vial was capped tightly, quickly sonicated and heated at 120° C. for 24 hours to yield a red solid. The mother solution was decanted and the powder was then washed thoroughly with DMF (3×5 mL) per day for 3 days, then soaked in anhydrous MeOH (3×5 mL) per day for 3 days total. The solvent-exchanged sample was desolvated under vacuum at ambient temperature for 24 hours, followed by heating at 100° C. under vacuum for an additional 24 hours to afford a blue-violet solid. Please refer back to step 2605 and step 2606 in FIG. 26.

Synthesis of Zn-VNU-93

Step 2605 and step 2606 are implemented by the following procedure. A 0.1 M stock solution of zinc nitrate hexahydrate ($Zn(NO_3)_2 \cdot 6H_2O$) in DMF was added to an 8 mL vial, which was preloaded with EDHB linker (0.114 mmol). This was followed by the addition of a mixture of $DMF:H_2O$ (v:v=3:1) to the vial. The vial was capped tightly, quickly sonicated and heated at 120° C. for 24 hours, yielding a light beige solid. The mother solution was decanted and the powder was then washed thoroughly with DMF (3×5 mL) per day for 3 days, then soaked in anhydrous MeOH (3×5 mL) per day for 3 days total. The solvent-exchanged sample was desolvated under vacuum at ambient temperature for 24 hours, followed by heating at 100° C. under vacuum for an additional 24 hours. Please refer back to step 2605 and step 2606 in FIG. 26.

Synthesis of Cu-VNU-93

Step 2605 and step 2606 are implemented by the following procedure. Under $N_2$ atmosphere, copper nitrate hexahydrate ($Cu(NO_3)_2 \cdot 3H_2O$) (0.375 mmol) and $H_4EHDB$ (0.15 mmol) were mounted in a 50 ml Schlenk tube. A solvent mixture of anhydrous DMF and anhydrous isopropanol (v:v=4:6) was then introduced to the tube via a syringe. The tube was thoroughly flash frozen at 77 K using liquid $N_2$ for 10 min, subsequently evacuated for 5 min to remove $O_2$. This process was repeated 3 times prior to filling with $N_2$, and the tube was kept under inert atmosphere via a balloon filled with $N_2$. The reaction mixture was refluxed at 100° C. for 45 minutes to produce greenish crystals. Consequently, the mother solution was decanted and the solid was washed with anhydrous DMF (3×5 mL) per day for 3 days, then soaked in anhydrous MeOH (3×5 mL) per day for 3 days total. The solvent-exchanged sample was desolvated under vacuum at ambient temperature for 24 hours, followed by heating at 100° C. under vacuum for an additional 24 hours. Please refer back to step 2605 and step 2606 in FIG. 26.

Synthesis of Fe-VNU-93

Step 2605 and step 2606 are implemented by the following procedure. The synthesis, solvent-exchange, and activation of Fe-VNU-93 were conducted under an inert atmosphere. Anhydrous ferrous chloride (0.09 mmol), $H_4EHDB$ (3.6 mmol), a mixture of anhydrous DMF and anhydrous MeOH (v:v=30:1) were added to a 25 mL Schlenk tube. This was followed by the addition of to the vial. The tube was thoroughly flash frozen at 77 K using liquid $N_2$ for 10 min, and subsequently evacuated for 5 min under vacuum to remove $O_2$. This process was repeated 3 times prior to filling with $N_2$, and the tube was kept under inert atmosphere via a balloon filled with $N_2$. The reaction mixture was then stirred and heated at 120° C. for 90 min to afford a brown-red precipitate. Consequently, the mother solution was decanted and the solid was washed with anhydrous DMF (3×5 mL) per day for 3 days, then soaked in anhydrous MeOH (3×5 mL) per day for 3 days total. The solvent-exchanged sample was desolvated under vacuum at ambient temperature for 24 hours, followed by heating at 65° C. under vacuum for an additional 24 hours.

4. Crystal Modeling

Crystal models were created through modification of the reported crystal structure of Mg-VNU-93. The atomic connectivity within the inorganic SBUs was kept the same. Water molecules were included to complete the octahedral coordination building of the metal atoms. The ethyne substituent group and phenyl rings were sketched in the original linker to obtain the $H_4EHDB$ linker. An energetic optimization was performed to achieve the geometry of the structures by using a smart algorithm and the universal force field implemented in the Forcite module of Material Studio. The initial R-3 space group was employed for all of the modelled structures. Subsequently, the unit cell parameters were optimized until the energy convergence criteria ($10^4$ kcal/mol) was obtained.

The formula was determined by elemental microanalysis of activated M-VNU-93 wherein coordinating water molecules were removed to leave the open metal sites. Pore aperture metrics of guest-free MOFs were measured by the distance between opposite metal-oxygen containing units of the hexagonal pore (atom to atom distance). The void volume of guest-free MOFs was determined by PLATON package using Calc Void function.

5. Powder X-Ray Diffraction Studies and Crystallography

Experimental powder X-ray diffraction (PXRD) patterns were collected on a Bruker D8 Advance, with Bragg Brentano geometry employing Ni-filtered Cu K$\alpha$ line ($\lambda$=1.54178 Å), focused radiation at 1600 W (40 kW, 40 mA) power and equipped with a Lynxeye detector. Samples were mounted on a zero background holder and then well-flatted the sample surface by a wide-blade spatula. PXRD measurements were conducted with the 2θ range from 3 to 50°, a step size of 0.02°, and a fixed count time of 1 s per step. The PXRD patterns of the experimental materials were measured at ambient temperature and pressure, and then compared with those calculated of the crystal models. Please refer back to FIG. 3-FIG. 8.

6. Gas Adsorption Measurements

Low-pressure $N_2$ and $CO_2$ adsorption isotherms were recorded on a Micromeritics 3Flex volumetric gas adsorption analyzer with an approximate 100 mg of activated MOF. A liquid-$N_2$ bath was used for measurements at 77 K, and a water circulator was used for measurements at 273 K, 283 K, and 298 K. The adsorbed amounts of $N_2$ gas at 77 K ($cm^3$ $g^{-1}$) are plotted to the relative pressures $P/P_0$. Accordingly, specific surface areas of IRMOFs were calculated based on the BET and Langmuir models. Moreover, pore size distributions (PSD) were estimated using a non-local density functional theory (NLDFT) based on an NLDFT (SD3), $N_2$-77-Carbon slit pores method equipped in Micromeritics software. The pore volume of activated MOF was estimated on the adsorption curves by using the BJH method. Please refer back to FIG. 15.

Detailed porosity of all MOFs was listed in Table 2. After the determination of permanent porosity for all MOFs, the $CO_2$ isotherms were explored at different temperatures of 273, 283, and 298 K. $CO_2$ uptakes at 298 K and 800 Torr were also listed in Table 2.

The coverage-dependent isosteric heat of adsorption ($Q_{st}$) of $CO_2$ was calculated by fitting the corresponding isotherms at 273 K, 283 K, and 298 K using a virial-type expansion equation. A Virial-type equation was employed for calculation of isoteric heat of adsorption ($Q_{st}$) (II):

$$\ln P = \ln N + \frac{1}{T}\sum_{i=0}^{m} a_i N^i + \sum_{i=0}^{n} b_i N^i \quad (II)$$

Where P is pressure, N is the adsorbed amount, T is temperature, ai and bi are virial coefficient, and m and n are the number of virial coefficients required for adequate fitting of the isotherms.

Accordingly, isosteric heat of adsorption ($Q_{st}$) at 298 K can be calculated (III):

$$= -R\sum_{i=0}^{m} a_i N^i.$$

Please refer to FIG. 22.

7. Catalytic Chemical Fixation of $CO_2$

Prior to implementing the catalytic reactions, the MOF platforms were activated to remove solvent molecules. All of the reactions were carried out in a 25 mL Schlenk tube equipped with a balloon pressure of $CO_2$.

In a typical reaction, under $N_2$ atmosphere, the activated MOFs (1.2 mol % ratio, based on the metal active sites), epoxide (styrene oxide, 5 mmol), and tetrabutylammonium bromide ($nBu_4NBr$, 1.5 mol %) were added to to Schlenk tube with a magnetic stirring bar. The mixture reaction was thoroughly evacuated to withdraw guest molecules; purged with $CO_2$ three times prior to maintaining a constant pressure of 1 atm via a balloon filled with $CO_2$, and finally heated to 80° C. for 6 hours.

After a certain time had elapsed, an aliquot of the reaction was taken and monitored by GC-MS. At the completion of the reaction, the resulting mixture was cooled to room temperature and the unreacted $CO_2$ was vented. The MOF catalysts were then separated by centrifugation, and an aliquot of the supernatant was analyzed by GC using biphenyl as the internal standard to determine the catalytic conversion, selectivity, and yield of the reaction.

The crude products were dissolved in diethyl ether (10 mL) and further extracted with water (3×10 mL). The diethyl ether layer was separated and concentrated in vacuo to obtain a white product. The purity of the carbonate product was confirmed by FT-IR, $^1H$ NMR, $^{13}C$ NMR, and GC-MS.

The M-VNU-93 catalyst was recycled by washing with DMF (3×5 mL) and MeOH (4×5 mL), followed by activated by thermal treatment under reduced pressure (same conditions used for the parent catalyst) prior to reuse in successive cycles.

In GC-MS the temperature program for GC-MS analysis was heated samples from 500 C for 2 min; heated from 50 to 3000° C. at 250° C./min; held at 3000° C. for 5 min. Inlet temperature was set at 2500° C. and He was used as carrier gas with the split flow 24.371 mL/min (split ratio 50:1).

The temperature program for GC-FID analysis heated samples from 50° C. for 2 min; heated from 50 to 250° C. at 25° C./min; held at 250° C. for 4 min. Inlet and detector temperature were set at 250 and 300° C., respectively. $N_2$ was used as carrier gas with the split flow 188.82 mL/min (split ratio 100:1). In back detector FID, $H_2$ and air flow were conducted with the split flow of 30 mL/min and 400 mL/min, respectively.

In GC-FID analysis, a multi-point internal standard method was used to determine the quantitation of each component in the mixture reaction. Each analysis contains the internal standard whose concentration is kept constant and the analyte of interest whose concentration covers the range of concentrations expected. The linear plot is the result with the ratio of the area of the analytes to that of the internal standard on the y-axis and the ratio of the concentration of the analytes to that of the internal standard on the x-axis. These data are fitted by a curve, corresponding to a standard equation for the further analysis of catalytic samples. In the samples with unknown analyte concentrations, determine the ratio of the analyte area to internal standard area from the GC-FID analysis. Accordingly, the corresponding ratio of analyte concentration to the internal standard concentration is determined from the standard graph.

In this work, calibration curves of epoxides/olefin and corresponding cyclic carbonates with the relationship between the ratio area of the substances and the ratio mole of the substances were created. Prior to each analysis, anhydrous EtOAc (1 mL) and biphenyl (0.135 g) were inserted and dissolved in an analyte sample. Accordingly, the plots of the epoxide/olefin and those of their corresponding carbonate products were created by GC-FID analysis.

INDUSTRIAL APPLICABILITY

The present disclosure provides a deprotection reaction of benzylic ether group; a synthetic procedure for synthesis of porous metal-organic frameworks with the same crystallographic structure by different metal sources including $Mg^{2+}$, $Ni^{2+}$, $Co^{2+}$, $Zn^{2+}$, $Cu^{2+}$, $Fe^{2+}$; a process for adsorbing carbon dioxide on porous metal-organic framework effectively under low pressure atmosphere; a process for producing cyclic carbonate catalyzed by metal-organic frameworks under ambient condition.

The following objects of the present invention are achieved.

A process for a multi-step synthesis of a Metal-Organic Framework that can adapt to different metal sites and therefore have different pore volumes that include:

(a) protecting of phenolic hydroxyl group using a benzylic ether (OBn) protection group through the reaction of hydroxy iodobenzoate and benzyl bromide (BnBr) for producing benzyloxy iodobenzoate compound;

(b) producing of ethyne bis(benzyloxybenzoate) compound by the Sonogashira cross-coupling method of benzyloxy iodobenzoate obtained in step (a);

(c) hydroxylating benzylic ether of bis(benzyloxybenzoate) compound obtained in step (b) by reacting with trimethylsilyl iodide (TMSI) for producing bis(hydroxybenzoate) compound;

(d) saponificating of bis(hydroxybenzoate) in a strong base solution for producing bis(hydroxybenzoic acid) compound;

(e) heating at elevated temperature liquid medium containing metal salt, bis(hydroxybenzoic acid) compound, a mixture of solvents in a sealed vial or an air-free tube under inert atmosphere for producing the as-synthesized Metal-Organic Framework (MOF);

(f) cooling liquid medium to room temperature, decanting the mother solution; and washing with anhydrous alcohol or anhydrous solvents for producing the solvent-exchanged Metal-Organic Framework (MOF).

(g) drying solvent-exchange Metal-Organic Framework (MOF) by vacuum under room temperature followed by heating at elevated temperature for producing the solvent-free Metal-Organic Framework (MOF).

A novel Metal-Organic Framework, which is a porous isostructural Metal-Organic Frameworks (MOFs), termed herein as M-VNU-93, wherein M comprises a metal ion (M=Mg, Ni, Co, Zn, Fe, Cu). M-VNU-93 exhibit selective $CO_2$ adsorption and efficiently catalytic activity for chemical fixation of $CO_2$ and epoxide in order to produce cyclic carbonate compounds.

A Metal-Organic Framework comprising bis(hydroxybenzoic acid) linking ligand.

A Metal-Organic Framework comprising bis(2-hydroxybenzoic acid) linking ligand, 4,4'-(ethyne-1,2-diyl)bis(2-hydroxybenzoic acid) linking ligand, and having a formula:

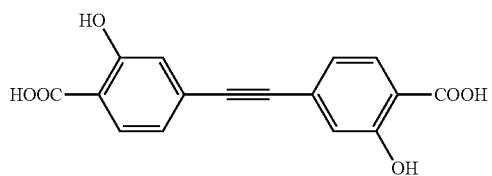

A Metal-Organic Framework comprising at least one divalent transition metal or alkaline earth metal such as magnesium, cobalt, nickel, zinc, copper, iron.

Another object of the present invention is to provide a Metal-Organic Framework comprising divalent transition metal or alkaline earth metal ion such as $Mg^{2+}$, $Co^{2+}$, $Ni^{2+}$, $Zn^{2+}$, $Cu^{2+}$, $Fe^{2+}$.

CONCLUSION

The above objects have industrial applications for $CO_2$ adsorption and chemical fixation of $CO_2$. A number of embodiments of the invention have been described. It will be understood that various details and modifications may be changed without departing from the scope of the disclosure. Accordingly, other embodiments are within the scope of the following chains.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should, therefore, be construed in accordance with the appended claims and any equivalents thereof.

ABBREVIATIONS

BnBr Benzyl Bromide
COOMe Methyl ester or methyl acetate ($COOCH_3$)
DBU 1,8-Diazabicyclo[5.4.0]undec-7-ene
DMF N, N-dimethylformamide
EDHB 4,4'-(ethyne-1,2 diyl) bis (2-hydroxybenzoic) acid
EDTA Ethylene diamine tretra acetic acid
FID Flame ionization detector
GC Gas chromatography
$K_2CO_3$ Potassium Carbonate
Me Methyl group ($CH_3$)
MeCN Acetonitrile ($CH_3$—CN)
NMR Nuclear Magnetic Resonance
Pd(PPh$_3$)$_2$Cl$_2$Bis(triphenylphosphine) palladium chloride
SBU Secondary Building Unit
SEM Scanning Electron Microscopy
FE-SEM Field-emission Scanning Electron Microscope
TEA Triethylamine
TMSI Trimethylsilyl iodide

REFERENCES

[1] Deng, H.; Grunder, S.; Cordova, K. E.; Valente, C.; Furukawa, H.; Hmadeh, M.; Gándara, F.; Whalley, A. C.; Liu, Z.; Asahina, S.; Kazumori, H.; O'Keeffe, M.; Terasaki, O.; Stoddart, J. F.; Yaghi, O. M. Large-Pore Apertures in a Series of Metal-Organic Frameworks. *Science* 2012, 336, 1018.

[2] Cho, H.-Y.; Yang, D.-A.; Kim, J.; Jeong, S.-Y.; Ahn, W.-S. $CO_2$ adsorption and catalytic application of Co-MOF-74 synthesized by microwave heating. *Catalysis Today* 2012, 185, 35-40.

[3] Yang, D.-A.; Cho, H.-Y.; Kim, J.; Yang, S.-T.; Ahn, W.-S. $CO_2$ capture and conversion using Mg-MOF-74 prepared by a sonochemical method. *Energy & Environmental Science* 2012, 5, 6465-6473.

[4] Nguyen, P. T. K.; Nguyen, H. T. D.; Nguyen, H. N.; Trickett, C. A.; Ton, Q. T.; Gutierrez-Puebla, E.; Monge, M. A.; Cordova, K. E.; Gándara, F. New Metal—Organic Frameworks for Chemical Fixation of $CO_2$. *ACS Applied Materials & Interfaces* 2018, 10, 733-744.

[5] Beyzavi, M. H.; Klet, R. C.; Tussupbayev, S.; Borycz, J.; Vermeulen, N. A.; Cramer, C. J.; Stoddart, J. F.; Hupp, J. T.; Farha, O. K. A hafnium-based metal-organic framework as an efficient and multifunctional catalyst for facile $CO_2$ fixation and regioselective and enantioretentive epoxide activation. *J Am Chem Soc* 2014, 136, 15861-15864.

[6] Jung, M. E.; Lyster, M. A. Quantitative dealkylation of alkyl ethers via treatment with trimethylsilyl iodide. A new method for ether hydrolysis. *The Journal of Organic Chemistry* 1977, 42, 3761-3764.

[7] Oh, H.; Maurer, S.; Balderas-Xicohtencatl, R.; Arnold, L.; Magdysyuk, O. V.; Schütz, G.; Müller, U.; Hirscher, M. Efficient synthesis for large-scale production and characterization for hydrogen storage of ligand exchanged MOF-74/174/184-M (M=$Mg^{2+}$, $Ni^{2+}$). *International Journal of Hydrogen Energy* 2017, 42, 1027-1035.

[8] Mio, M. J.; Kopel, L. C.; Braun, J. B.; Gadzikwa, T. L.; Hull, K. L.; Brisbois, R. G.; Markworth, C. J.; Grieco, P. A. One-Pot Synthesis of Symmetrical and Unsymmetrical Bisarylethynes by a Modification of the Sonogashira Coupling Reaction. *Organic Letters* 2002, 4, 3199-3202.

What is claimed is:

1. A Zn-VNU-93 MOF (Metal-Organic Framework), comprising:
   an organic linking ligand having a structural formula:

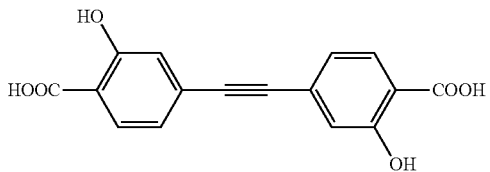 [SMILES: O=C(O)c1ccc(C#Cc2ccc(C(=O)O)c(O)c2)cc1O]

and
   a Zinc ion ($Zn^{2+}$), wherein said Zn-VNU-93 MOF is manufactured by a process comprising the steps of:
   (a) protecting of a phenolic hydroxyl group using benzylic ether (OBn) through a reaction of hydroxy iodobenzoate and benzyl bromide (BnBr) for producing a benzyloxy iodobenzoate compound;
   (b) producing an ethyne bis(benzyloxybenzoate) compound by Sonogashira cross-coupling of benzyloxy iodobenzoate compound obtained in said step (a);
   (c) hydroxylating benzylic ether of a bis(benzyloxybenzoate) compound obtained in said step (b) by reacting with an organosilicon compound for producing bis(hydroxybenzoate) compound;
   (d) saponificating of said bis(hydroxybenzoate) in a strong base solution for producing a bis(hydroxybenzoic acid) compound;
   (e) adding Zinc nitrate hexahydrate ($Zn(NO_3)_2.6H_2O$), and heating at an elevated temperature a liquid medium containing Zinc nitrate hexahydrate ($Zn(NO_3)_2.6H_2O$) said bis(hydroxybenzoic acid) compound, and a mixture of solvents in a sealed vial or an air-free tube under inert atmosphere producing the as-synthesized Metal-Organic Framework (MOF);
   (f) cooling liquid medium to room temperature, decanting the mother solution; and washing said light beige solid with DMF and anhydrous methanol for producing a solvent-exchanged Zn-VNU-93 MOF; and
   (g) drying said solvent-exchange Zn-VNU-93 MOF by vacuum under room temperature followed by heating at 100° C. for producing a solvent-free Zn-VNU-93 MOF so that said Zn-VNU-93 MOF is characterized by following properties:
   a BET surface area of 2,790 $m^2g^-$, a pore volume of 0.23 $cm^3g-1$, and capable of adsorbing carbon dioxide ($CO_2$) at 39.4 $cm^3g^{-1}$;
   a crystal dimension specified as 41.1456 angstroms (Å) and 5.5642 angstroms (Å) and a unit cell volume of 9,685,613 angstroms (Å);
   a plurality of mesopores, each having a diameter of 22.6 angstroms (Å);
   a density of 0.7785 $g/cm^3$;
   a void volume of 70.2% of the total volume of said Zn-VNU-93;
   a capacity to act as a catalyst in a carbon dioxide ($CO_2$) conversion process to styrene carbonate and styrene; and
   a carbon dioxide conversion rate of 74%.

2. The Zn-VNU-93 Metal-Organic Framework of claim 1 wherein said organosilicon compound is trimethylsilyl iodide (TMSI).

3. The Zn-VNU-93 MOF of claim 1 wherein said organic linking ligand is synthesized by a process comprising a protection step, a cross-coupling step, a cleavage step, and a deprotection step.

4. The Zn-VNU-93 MOF of claim 1 further characterized as having crystalline structure.

5. The Zn-VNU-93 MOF of claim 1 further characterized as having a Langmuir surface area of 3,028 $m^2/g^{-1}$.

6. The Zn-VNU-93 MOF of claim 1 further characterized as having adsorbing carbon dioxide ($CO_2$) varies linearly with pressure.

7. The Zn-VNU-93 MOF of claim 6 further characterized as having adsorbing carbon dioxide ($CO_2$) decreases with an increase in temperature.

8. The Zn-VNU-93 MOF of claim 1 wherein said capacity to act as a catalyst in a carbon dioxide ($CO_2$) conversion process of styrene oxide to styrene carbonate with a conversion rate of 96%, a selectivity rate of 79%, and a yield of 76%.

9. The Zn-VNU-93 MOF of claim 8 wherein said $CO_2$ conversion process of styrene oxide to styrene carbonate using said Zn-VNU-93 as said catalyst is a cycloaddition reaction performed at $CO_2$ at 1 atm pressure, 1.5 mole % of $nBu_4NBr$ at 80° C. and for 6 hours.

10. A process for synthesizing a Zn-VNU-93 Metal-Organic Framework (MOF), comprising:
   (a) protecting of phenolic hydroxyl group using benzylic ether (OBn) through the reaction of hydroxy iodobenzoate and benzyl bromide (BnBr) for producing a benzyloxy iodobenzoate compound;
   (b) producing of an ethyne bis(benzyloxybenzoate) compound by Sonogashira cross-coupling of benzyloxy iodobenzoate compound obtained in said step (a);
   (c) hydroxylating benzylic ether of a bis(benzyloxybenzoate) compound obtained in said step (b) by reacting with an organosilicon compound for producing bis(hydroxybenzoate) compound;

(d) saponificating of said bis(hydroxybenzoate) in a strong base solution for producing a bis(hydroxybenzoic) acid compound;
(e) adding Zinc nitrate hexahydrate ($Zn(NO_3)_2 \cdot 6H_2O$), and heating at an elevated temperature a liquid medium containing Zinc nitrate hexahydrate ($Zn(NO_3)_2 \cdot 6H_2O$), said bis(hydroxybenzoic acid) compound, and a mixture of solvents in a sealed vial or an air-free tube under inert atmosphere producing a synthesized Metal-Organic Framework (MOF);
(f) cooling liquid medium to room temperature, decanting the mother solution; and washing said light beige Zn-VNU-93 MOF with DMF and anhydrous methanol for producing a solvent-exchanged Zn-VNU-93 MOF; and
(g) drying said solvent-exchange Zn-VNU-93 MOF by vacuum under room temperature followed by heating at 100° C. for producing a solvent-free Zn-VNU-93 MOF wherein after said steps (a) to (g) said Zn-VNU-93 MOF is characterized by following properties:
a BET surface area of 2,790 $m^2g^{-1}$, a pore volume of 0.23 $cm^3g-1$, and capable of adsorbing carbon dioxide ($CO_2$) at 39.4 $cm^3g^{-1}$;
a crystal dimension specified as 41.1456 angstroms (Å) and 5.5642 angstroms (Å) and a unit cell volume of 9,685,613 angstroms (Å);
a plurality of mesopores, each having a diameter of 22.6 angstroms (Å);
a density of 0.7785 $g/cm^3$;
a void volume of 70.2% of the total volume of said Zn-VNU-93;
a capacity to act as a catalyst in a carbon dioxide ($CO_2$) conversion process to styrene carbonate from styrene oxide; and
a carbon dioxide conversion rate of 74%.

11. The process of claim 10, wherein said organosilicon compound is trimethylsilyl iodide (TMSI).

12. The process of claim 10, wherein said bis(hydroxybenzoic acid) compound is bis(2-hydroxybenzoic acid).

13. The process of claim 10, wherein said bis(hydroxybenzoic acid) compound is 4,4'-(ethyne-1,2-diyl)bis(2-hydroxybenzoic acid) having a formula

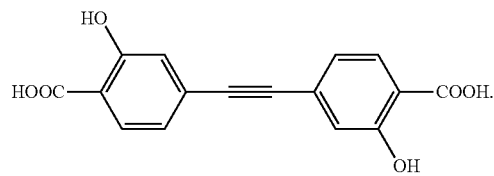

14. The process of claim 10 wherein said step (a) of protecting of phenolic hydroxyl group further comprises using potassium carbonate ($K_2CO_3$) and benzylic ether (OBn) as reagents.

15. The process of claim 10 wherein said step (a) of protecting of phenolic hydroxyl group further comprises using acetonitrile (MeCN) as a solvent temperature of 80° C. for 24 hours.

16. The process of claim 10 wherein said step (b) of cross-coupling further comprises using palladium (Pd) and copper (Cu) as cocatalyst.

17. The process of claim 10 wherein said step (c) further comprising using dicloromethane ($CH_2Cl_2$) as solvent.

18. The process of claim 17 wherein said base solution in said step (d) comprises is sodium hydroxide (NaOH) which is added in a solution of said bis(hydroxybenzoate) compound in a tetrahydrofuran/methanol (THF/MeOH) solution which is stirred at 60° C. for 24 hours and acidified with one mole of hydrochloride acid (HCl) to obtain said organic linking ligand.

19. The process of claim 10 wherein said mixture of solvents in said step (e) further comprises adding a solution of dimethylformamide and water at a volume ration of 3 to 1 ($DMF:H_2O$ at v:v=3:1) into a sealed vial preloaded with 0.114 mmol of said bis(hydroxybenzoic acid) compound.

20. The process of claim 10 wherein said sealed vial containing said bis(hydroxybenzoic acid) compound and $DMF:H_2O$ solution is sonicated at 120° C. for 24 hours to obtain a light beige solid which is then washed with dimethylformamide (DMF) and soaked in MeOH, and desolated at ambient temperature, and finally followed by heating at said elevated temperature at 100° C.

* * * * *